(12) United States Patent
Gambale

(10) Patent No.: US 8,551,120 B2
(45) Date of Patent: *Oct. 8, 2013

(54) TISSUE CAPTURING AND SUTURING DEVICE AND METHOD

(75) Inventor: Richard A. Gambale, Tyngsboro, MA (US)

(73) Assignee: C.R. Bard, Inc., Murray Hill, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/613,366

(22) Filed: Sep. 13, 2012

(65) Prior Publication Data

US 2013/0018394 A1    Jan. 17, 2013

Related U.S. Application Data

(63) Continuation of application No. 12/070,673, filed on Feb. 20, 2008, now Pat. No. 8,388,632, which is a continuation of application No. 11/803,956, filed on May 16, 2007, now Pat. No. 7,951,157, which is a continuation of application No. 10/275,534, filed as application No. PCT/US01/16025 on May 19, 2001, now Pat. No. 7,220,266.

(60) Provisional application No. 60/205,444, filed on May 19, 2000, provisional application No. 60/205,741, filed on May 19, 2000, provisional application No. 60/253,970, filed on Nov. 29, 2000.

(30) Foreign Application Priority Data

Mar. 5, 2001  (WO) ............... PCT/US01/07349

(51) Int. Cl.
*A61B 17/04* (2006.01)
*A61B 17/10* (2006.01)

(52) U.S. Cl.
USPC ............ 606/144; 606/139; 606/153

(58) Field of Classification Search
USPC ................... 606/139, 142, 144, 148
See application file for complete search history.

(56) References Cited

U.S. PATENT DOCUMENTS

| 3,868,448 A | 2/1975 | Hahn et al. |
| 4,133,315 A | 1/1979 | Berman et al. |

(Continued)

FOREIGN PATENT DOCUMENTS

| EP | 0 571 938 B1 | 12/1993 |
| EP | 1 397 998 A1 | 3/2004 |

(Continued)

OTHER PUBLICATIONS

Awan, A., et al., "Endoscopic Vertical Band Gastroplasty with an Endoscopic Sewing Machine", Gastrointestinal Endoscopy (2002) pp. 254-256, vol. 55, No. 2.

(Continued)

*Primary Examiner* — Julian W Woo
(74) *Attorney, Agent, or Firm* — Wolf, Greenfield & Sacks, P.C.

(57) ABSTRACT

A combination tissue apposition and suture capturing device (100) for performing endoscopic procedures typically in the gastro-esophageal tract. The device (100) is particularly adapted for forming multiple plications used in a gastroplasty procedure devised to cure or ameliorate gastro-esophageal reflux disease. The device include a tissue sewing capsule (102) attached to the distal end of an endoscope having a needle (120) that is deposited in a capsule (102) distal tip cavity following the suturing of a tissue fold and retrieved to enable the suturing of a subsequent tissue fold without the need for multiple intubations. A suture clip delivery device (200) is also disclosed that is adapted to fit within the capsule to enable suture capture without the need for multiple intubations. The combination device eliminates the need for an overtube and maximizes the speed efficiency of the gastroplasty procedure. A method for using the combination device is also disclosed.

10 Claims, 29 Drawing Sheets

(56) References Cited

U.S. PATENT DOCUMENTS

| | | |
|---|---|---|
| 4,235,238 A | 11/1980 | Ogiu et al. |
| 4,246,893 A | 1/1981 | Berson |
| 4,403,604 A | 9/1983 | Wilkinson et al. |
| 4,416,267 A | 11/1983 | Garren et al. |
| 4,694,827 A | 9/1987 | Weiner et al. |
| 4,739,758 A | 4/1988 | Lai et al. |
| 4,803,985 A | 2/1989 | Hill |
| 4,841,888 A | 6/1989 | Mills et al. |
| 4,899,747 A | 2/1990 | Garren et al. |
| 5,037,021 A | 8/1991 | Mills et al. |
| 5,080,663 A | 1/1992 | Mills et al. |
| 5,084,061 A | 1/1992 | Gau et al. |
| 5,234,454 A | 8/1993 | Bangs |
| 5,250,053 A | 10/1993 | Snyder |
| 5,259,399 A | 11/1993 | Brown |
| 5,322,697 A | 6/1994 | Meyer |
| 5,327,914 A | 7/1994 | Shlain |
| 5,345,949 A | 9/1994 | Shlain |
| 5,355,897 A | 10/1994 | Pietrafitta et al. |
| 5,423,872 A | 6/1995 | Cigaina |
| 5,474,565 A | 12/1995 | Trott |
| 5,549,621 A | 8/1996 | Bessler et al. |
| 5,562,689 A | 10/1996 | Green et al. |
| 5,571,116 A | 11/1996 | Bolanos et al. |
| 5,584,835 A | 12/1996 | Greenfield |
| 5,626,590 A | 5/1997 | Wilk |
| 5,665,376 A | 9/1997 | Russo |
| 5,792,153 A | 8/1998 | Swain et al. |
| 5,820,584 A | 10/1998 | Crabb |
| 5,868,141 A | 2/1999 | Ellias |
| 5,868,760 A | 2/1999 | McGuckin |
| 5,887,594 A | 3/1999 | LoCicero, III |
| 5,910,105 A | 6/1999 | Swain et al. |
| 5,938,668 A | 8/1999 | Scirica et al. |
| 5,977,175 A | 11/1999 | Lin |
| 6,009,877 A | 1/2000 | Edwards |
| 6,044,846 A | 4/2000 | Edwards |
| 6,083,150 A | 7/2000 | Aznoian et al. |
| 6,092,528 A | 7/2000 | Edwards |
| 6,097,984 A | 8/2000 | Douglas |
| 6,102,922 A | 8/2000 | Jakobsson et al. |
| 6,139,555 A | 10/2000 | Hart et al. |
| 6,234,955 B1 | 5/2001 | Silverman et al. |
| 6,238,335 B1 | 5/2001 | Silverman et al. |
| 6,248,058 B1 | 6/2001 | Silverman et al. |
| 6,251,063 B1 | 6/2001 | Silverman et al. |
| 6,251,064 B1 | 6/2001 | Silverman et al. |
| 6,352,503 B1 | 3/2002 | Matsui et al. |
| 6,358,259 B1 | 3/2002 | Swain et al. |
| 6,398,795 B1 | 6/2002 | McAlister et al. |
| 6,405,732 B1 | 6/2002 | Edwards et al. |
| 6,427,089 B1 | 7/2002 | Knowlton |
| 6,447,533 B1 | 9/2002 | Adams |
| 6,494,888 B1 | 12/2002 | Laufer et al. |
| 6,530,878 B2 | 3/2003 | Silverman et al. |
| 6,533,717 B2 | 3/2003 | Silverman et al. |
| 6,535,764 B2 | 3/2003 | Imran et al. |
| 6,540,789 B1 | 4/2003 | Silverman et al. |
| 6,543,456 B1 | 4/2003 | Freeman |
| 6,558,400 B2 | 5/2003 | Deem et al. |
| 6,562,034 B2 | 5/2003 | Edwards et al. |
| 6,572,627 B2 | 6/2003 | Gabbay |
| 6,572,629 B2 | 6/2003 | Kalloo et al. |
| 6,575,896 B2 | 6/2003 | Silverman et al. |
| 6,589,238 B2 | 7/2003 | Edwards et al. |
| 6,591,838 B2 | 7/2003 | Durgin |
| 6,592,596 B1 | 7/2003 | Geitz |
| 6,595,909 B2 | 7/2003 | Silverman et al. |
| 6,595,910 B2 | 7/2003 | Silverman et al. |
| 6,600,953 B2 | 7/2003 | Flesler et al. |
| 6,605,294 B2 | 8/2003 | Sawhney |
| 6,608,029 B1 | 8/2003 | Kolterman et al. |
| 6,613,047 B2 | 9/2003 | Edwards |
| 6,615,084 B1 | 9/2003 | Cigaina |
| 6,627,206 B2 | 9/2003 | Lloyd |
| 6,663,639 B1 | 12/2003 | Laufer et al. |
| 6,675,809 B2 | 1/2004 | Stack et al. |
| 6,712,814 B2 | 3/2004 | Edwards et al. |
| 6,716,222 B2 | 4/2004 | McAlister et al. |
| 6,736,828 B1 | 5/2004 | Adams et al. |
| 6,740,082 B2 | 5/2004 | Shadduck |
| 6,740,121 B2 | 5/2004 | Geitz |
| 6,749,607 B2 | 6/2004 | Edwards et al. |
| 6,755,869 B2 | 6/2004 | Geitz |
| 6,758,219 B2 | 7/2004 | Sapala et al. |
| 6,773,440 B2 | 8/2004 | Gannoe |
| 6,773,441 B1 | 8/2004 | Laufer et al. |
| 6,802,841 B2 | 10/2004 | Utley et al. |
| 6,802,868 B2 | 10/2004 | Silverman et al. |
| 6,845,776 B2 | 1/2005 | Stack et al. |
| 6,846,312 B2 | 1/2005 | Edwards et al. |
| 6,858,576 B1 | 2/2005 | Young et al. |
| 6,866,663 B2 | 3/2005 | Edwards et al. |
| 6,901,295 B2 | 5/2005 | Sharma |
| 6,916,332 B2 | 7/2005 | Adams |
| 6,955,643 B2 | 10/2005 | Gellman |
| 6,981,978 B2 | 1/2006 | Gannoe |
| 6,986,737 B2 | 1/2006 | Suzuki et al. |
| 6,997,931 B2 | 2/2006 | Sauer |
| 7,033,373 B2 | 4/2006 | de la Torre et al. |
| 7,037,315 B2 | 5/2006 | Sancoff et al. |
| 7,037,343 B2 | 5/2006 | Imran |
| 7,037,344 B2 | 5/2006 | Kagan et al. |
| 7,083,630 B2 | 8/2006 | DeVries et al. |
| 7,090,684 B2 | 8/2006 | McGuckin et al. |
| 7,125,413 B2 | 10/2006 | Grigoryants |
| 7,152,607 B2 | 12/2006 | Stack et al. |
| 7,175,638 B2 | 2/2007 | Gannoe et al. |
| 7,175,669 B2 | 2/2007 | Geitz |
| 7,201,757 B2 | 4/2007 | Knudson et al. |
| 7,204,842 B2 | 4/2007 | Geitz |
| 7,220,284 B2 | 5/2007 | Kagan et al. |
| 7,229,428 B2 | 6/2007 | Gannoe |
| 7,238,191 B2 | 7/2007 | Bachmann |
| 7,239,912 B2 | 7/2007 | Dobak |
| 7,316,716 B2 | 1/2008 | Egan |
| 7,431,725 B2 | 10/2008 | Stack et al. |
| 7,503,922 B2 | 3/2009 | Deem et al. |
| 7,510,559 B2 | 3/2009 | Deem et al. |
| 7,520,884 B2 | 4/2009 | Swanstrom |
| 7,666,195 B2 | 2/2010 | Kelleher et al. |
| 7,691,152 B2 | 4/2010 | Silverman |
| 7,704,264 B2 | 4/2010 | Ewers |
| 7,736,372 B2 | 6/2010 | Reydel |
| 7,736,373 B2 | 6/2010 | Laufer |
| 7,737,109 B2 | 6/2010 | Miller |
| 8,088,132 B2 | 1/2012 | Roslin |
| 8,152,821 B2 | 4/2012 | Gambale et al. |
| 8,172,857 B2 | 5/2012 | Fogel |
| 2001/0011543 A1 | 8/2001 | Forsell et al. |
| 2002/0022851 A1 | 2/2002 | Kalloo et al. |
| 2002/0055750 A1 | 5/2002 | Durgin et al. |
| 2002/0055757 A1 | 5/2002 | Torre et al. |
| 2002/0065523 A1 | 5/2002 | McAlister et al. |
| 2002/0082616 A1 | 6/2002 | McAlister et al. |
| 2002/0082621 A1 | 6/2002 | Schurr et al. |
| 2002/0107530 A1 | 8/2002 | Sauer et al. |
| 2002/0115991 A1 | 8/2002 | Edwards |
| 2002/0139379 A1 | 10/2002 | Edwards et al. |
| 2002/0143346 A1 | 10/2002 | McGuckin et al. |
| 2002/0161414 A1 | 10/2002 | Flesler et al. |
| 2002/0169357 A1 | 11/2002 | Chen |
| 2002/0183765 A1 | 12/2002 | Adams |
| 2002/0183768 A1 | 12/2002 | Deem et al. |
| 2002/0188354 A1 | 12/2002 | Peghini |
| 2002/0193816 A1 | 12/2002 | Laufer et al. |
| 2003/0009165 A1 | 1/2003 | Edwards et al. |
| 2003/0014086 A1 | 1/2003 | Sharma |
| 2003/0021822 A1 | 1/2003 | Lloyd |
| 2003/0024538 A1 | 2/2003 | Edwards et al. |
| 2003/0078466 A1 | 4/2003 | Silverman |
| 2003/0109892 A1 | 6/2003 | Deem et al. |
| 2003/0113310 A1 | 6/2003 | Van Laere et al. |
| 2003/0120321 A1 | 6/2003 | Bumm |

| | | |
|---|---|---|
| 2003/0135206 A1 | 7/2003 | Edwards et al. |
| 2003/0139752 A1 | 7/2003 | Pasricha et al. |
| 2003/0144708 A1 | 7/2003 | Starkebaum |
| 2003/0158601 A1 | 8/2003 | Silverman et al. |
| 2003/0161887 A1 | 8/2003 | Klein |
| 2003/0171760 A1 | 9/2003 | Gambale |
| 2003/0181925 A1 | 9/2003 | Bain et al. |
| 2003/0181958 A1 | 9/2003 | Dobak, III |
| 2003/0188755 A1 | 10/2003 | Milbocker |
| 2003/0195509 A1 | 10/2003 | Edwards et al. |
| 2003/0208209 A1 | 11/2003 | Gambale et al. |
| 2003/0220660 A1 | 11/2003 | Kortenbach et al. |
| 2003/0233108 A1 | 12/2003 | Gellman et al. |
| 2003/0236536 A1 | 12/2003 | Grigoryants et al. |
| 2004/0006351 A1 | 1/2004 | Gannoe et al. |
| 2004/0009224 A1 | 1/2004 | Miller |
| 2004/0015201 A1 | 1/2004 | Greenstein |
| 2004/0019388 A1 | 1/2004 | Starkebaum |
| 2004/0030217 A1 | 2/2004 | Yeung |
| 2004/0037865 A1 | 2/2004 | Miller |
| 2004/0039452 A1 | 2/2004 | Bessler |
| 2004/0044353 A1 | 3/2004 | Gannoe |
| 2004/0044354 A1 | 3/2004 | Gannoe et al. |
| 2004/0044376 A1 | 3/2004 | Flesler et al. |
| 2004/0059289 A1 | 3/2004 | Garza Alvarez |
| 2004/0082859 A1 | 4/2004 | Schaer |
| 2004/0082950 A1 | 4/2004 | Edwards et al. |
| 2004/0082963 A1 | 4/2004 | Gannoe et al. |
| 2004/0087976 A1 | 5/2004 | DeVries et al. |
| 2004/0087977 A1 | 5/2004 | Nolan et al. |
| 2004/0089313 A1 | 5/2004 | Utley et al. |
| 2004/0092892 A1 | 5/2004 | Kagan et al. |
| 2004/0096514 A1 | 5/2004 | Vogel et al. |
| 2004/0097415 A1 | 5/2004 | Kolterman et al. |
| 2004/0097986 A1 | 5/2004 | Adams |
| 2004/0097989 A1 | 5/2004 | Molina Trigueros |
| 2004/0116949 A1 | 6/2004 | Ewers et al. |
| 2004/0117031 A1 | 6/2004 | Stack et al. |
| 2004/0122456 A1 | 6/2004 | Saadat et al. |
| 2004/0122470 A1 | 6/2004 | Deem et al. |
| 2004/0122473 A1 | 6/2004 | Ewers et al. |
| 2004/0122526 A1 | 6/2004 | Imran |
| 2004/0133147 A1 | 7/2004 | Woo et al. |
| 2004/0133220 A1 | 7/2004 | Lashinski et al. |
| 2004/0138744 A1 | 7/2004 | Lashinski et al. |
| 2004/0147921 A1 | 7/2004 | Edwards et al. |
| 2004/0153146 A1 | 8/2004 | Lashinski |
| 2004/0158263 A1 | 8/2004 | McAlister et al. |
| 2004/0162567 A9 | 8/2004 | Adams |
| 2004/0162568 A1 | 8/2004 | Saadat et al. |
| 2004/0167546 A1 | 8/2004 | Saadat |
| 2004/0186502 A1 | 9/2004 | Sampson |
| 2004/0193190 A1 | 9/2004 | Liddicoat et al. |
| 2004/0194157 A1 | 9/2004 | Meguid |
| 2004/0194790 A1 | 10/2004 | Laufer et al. |
| 2004/0199180 A1 | 10/2004 | Knodel et al. |
| 2004/0204708 A1 | 10/2004 | Edwards et al. |
| 2004/0210243 A1 | 10/2004 | Gannoe et al. |
| 2004/0215180 A1 | 10/2004 | Starkebaum |
| 2004/0220682 A1 | 11/2004 | Levine et al. |
| 2004/0225183 A1 | 11/2004 | Michlitsch et al. |
| 2004/0225305 A1 | 11/2004 | Ewers |
| 2004/0236356 A1 | 11/2004 | Rioux et al. |
| 2004/0248188 A1 | 12/2004 | Sanders |
| 2004/0258621 A1 | 12/2004 | Stern |
| 2004/0260316 A1 | 12/2004 | Knudson et al. |
| 2004/0267378 A1 | 12/2004 | Gazi |
| 2005/0022827 A1 | 2/2005 | Woo et al. |
| 2005/0024222 A1 | 2/2005 | Nelson |
| 2005/0033319 A1 | 2/2005 | Gambale et al. |
| 2005/0033320 A1 | 2/2005 | McGuckin et al. |
| 2005/0033331 A1 | 2/2005 | Burnett et al. |
| 2005/0033332 A1 | 2/2005 | Burnett |
| 2005/0043817 A1 | 2/2005 | McKenna |
| 2005/0049614 A1 | 3/2005 | Cendan |
| 2005/0055038 A1 | 3/2005 | Kelleher et al. |
| 2005/0055039 A1 | 3/2005 | Burnett et al. |
| 2005/0060030 A1 | 3/2005 | Lashinski et al. |
| 2005/0065536 A1 | 3/2005 | Ewers et al. |
| 2005/0075653 A1 | 4/2005 | Saadat et al. |
| 2005/0080444 A1 | 4/2005 | Kramer et al. |
| 2005/0085829 A1 | 4/2005 | Kraemer et al. |
| 2005/0085923 A1 | 4/2005 | Levine et al. |
| 2005/0090837 A1 | 4/2005 | Sixto et al. |
| 2005/0090873 A1 | 4/2005 | Imran |
| 2005/0119671 A1 | 6/2005 | Reydel et al. |
| 2005/0119674 A1 | 6/2005 | Gingras |
| 2005/0137643 A1 | 6/2005 | Mintchev |
| 2005/0143760 A1 | 6/2005 | Imran |
| 2005/0149067 A1 | 7/2005 | Takemoto et al. |
| 2005/0149072 A1 | 7/2005 | DeVries et al. |
| 2005/0149200 A1 | 7/2005 | Silverman et al. |
| 2005/0154405 A1 | 7/2005 | Kraemer et al. |
| 2005/0159743 A1 | 7/2005 | Edwards et al. |
| 2005/0171556 A1 | 8/2005 | Murphy |
| 2005/0177176 A1 | 8/2005 | Gerbi et al. |
| 2005/0192614 A1 | 9/2005 | Binmoeller |
| 2005/0216036 A1 | 9/2005 | Nakao |
| 2005/0222492 A1 | 10/2005 | Adams |
| 2005/0246037 A1 | 11/2005 | Starkebaum |
| 2005/0251162 A1 | 11/2005 | Rothe et al. |
| 2005/0256587 A1 | 11/2005 | Egan |
| 2005/0267499 A1 | 12/2005 | Stack et al. |
| 2006/0020277 A1 | 1/2006 | Gostout et al. |
| 2006/0020278 A1 | 1/2006 | Burnett et al. |
| 2006/0047289 A1 | 3/2006 | Fogel |
| 2006/0149316 A1 | 7/2006 | DeVries et al. |
| 2006/0212053 A1 | 9/2006 | Gertner |
| 2006/0264983 A1 | 11/2006 | Holsten et al. |
| 2006/0276812 A1 | 12/2006 | Hill et al. |
| 2006/0282087 A1 | 12/2006 | Binmoeller |
| 2007/0032702 A1 | 2/2007 | Ortiz |
| 2007/0032800 A1 | 2/2007 | Ortiz et al. |
| 2007/0049929 A1 | 3/2007 | Catanese, III et al. |
| 2007/0055292 A1 | 3/2007 | Ortiz et al. |
| 2007/0129735 A1 | 6/2007 | Filipi et al. |
| 2007/0129738 A1 | 6/2007 | Kraemer et al. |
| 2007/0167963 A1 | 7/2007 | Deem et al. |
| 2007/0173931 A1 | 7/2007 | Tremulis et al. |
| 2007/0175488 A1 | 8/2007 | Cox et al. |
| 2008/0154289 A1 | 6/2008 | Roslin |
| 2008/0161787 A1 | 7/2008 | Roslin |
| 2008/0215069 A1 | 9/2008 | Gambale et al. |
| 2008/0249538 A1 | 10/2008 | Kraemer et al. |
| 2009/0088780 A1 | 4/2009 | Shiono et al. |
| 2009/0088796 A1 | 4/2009 | Abbott et al. |
| 2010/0137885 A1 | 6/2010 | Ortiz |

FOREIGN PATENT DOCUMENTS

| | | |
|---|---|---|
| EP | 1 414 378 B1 | 5/2004 |
| EP | 1 749 480 A1 | 2/2007 |
| EP | 1 749 482 A2 | 2/2007 |
| EP | 1 759 639 A1 | 3/2007 |
| EP | 1 815 805 B1 | 8/2007 |
| GB | 1 174 814 | 12/1969 |
| WO | WO 93/20819 | 10/1993 |
| WO | WO 95/25468 A1 | 9/1995 |
| WO | WO 95/32670 A1 | 12/1995 |
| WO | WO 97/30639 A1 | 8/1997 |
| WO | WO 99/04698 A1 | 2/1999 |
| WO | WO 99/04699 A1 | 2/1999 |
| WO | WO 99/35987 | 7/1999 |
| WO | WO 99/60931 | 12/1999 |
| WO | WO 00/48672 | 8/2000 |
| WO | WO 01/26588 | 4/2001 |
| WO | WO 01/66020 | 9/2001 |
| WO | WO 02/060328 | 8/2002 |
| WO | WO 02/096327 | 12/2002 |
| WO | WO 03/051391 | 6/2003 |
| WO | WO 03/086247 | 10/2003 |
| WO | WO 03/094785 | 11/2003 |
| WO | WO 2004/019765 A2 | 3/2004 |
| WO | WO 2004/021894 | 3/2004 |
| WO | WO 2004/017863 | 4/2004 |
| WO | WO 2004/034973 | 4/2004 |
| WO | WO 2004/069056 A1 | 8/2004 |
| WO | WO 2004/075974 | 9/2004 |
| WO | WO 2004/084808 | 10/2004 |

| WO | WO 2004/103189 A1 | 12/2004 |
| WO | WO 2004/112563 | 12/2004 |
| WO | WO 2005/011463 | 2/2005 |
| WO | WO 2005/011519 | 2/2005 |
| WO | WO 2005/020802 | 3/2005 |
| WO | WO 2005/037072 | 4/2005 |
| WO | WO 2005/037152 | 4/2005 |
| WO | WO 2005/039458 | 5/2005 |
| WO | WO 2005/058239 | 6/2005 |
| WO | WO 2007/019268 A2 | 2/2007 |
| WO | WO 2007/095096 A2 | 8/2007 |
| WO | WO 2009/042816 A2 | 4/2009 |
| WO | WO 2010/021743 A1 | 2/2010 |

OTHER PUBLICATIONS

Awan, A., et al., "Endoscopic Vertical Band Gastroplasty (VBG) with Outlet Ring Using Endoscopic Sewing Machine", Gastroenterology (Apr. 2000) vol. 118, No. 4, Suppl. 2, Abstract 4131.

Schwartz, R., et al., "Gastric Bypass Revision: Lessons Learned From 920 Cases", Surgery (Oct. 1988) pp. 806-812, vol. 104, No. 4.

Schweitzer, M., "Endoscopic Intraluminal Suture Plication of the Gastric Pouch and Stoma in Postoperative Roux-en-Y Gastric Bypass Patients", Journal of Laparoendoscopic & Advanced Surgical Techniques (2004) pp. 223-226, vol. 14, No. 4.

Spaulding, L., "Treatment of Dilated Gastrojejunostomy with Sclerotherapy", Obesity Surgery (2003) pp. 254-257, vol. 13.

Sugerman, H., "Bariatric Surgery for Severe Obesity", Journal of the Association for Academic Minority Physicians (Jul. 2001) pp. 129-136, vol. 12, No. 3.

Kirkpatrick, J., et al., "Critical Determinants of a Successful Gastric Bypass: Reservoir Versus Stoma", American Journal of Gastroenterology (1982) pp. 464-466, vol. 77, No. 7.

Lundell, L., et al., "Measurement of Pouch Volume and Stoma Diameter After Gastroplasty", International Journal of Obesity (1987) pp. 169-174, vol. 11.

Miskowiak, J., et al., "Radiologic Findings and Weight Loss Following Gastroplasty for Morbid Obesity", Acta Radiologica Diagnosis (1986) pp. 553-555, vol. 27.

Reinhold, D., et al., "The Role of Dipeptidyl Peptidase IV (DP IV) Enzymatic Activity in T Cell Activation and Autoimmunity", Biol. Chem. (Jul./Aug. 2002) pp. 1133-1138, vol. 383.

Rutledge, R., et al., "Continued Excellent Results with the Mini-Gastric Bypass: Six-Year Study in 2,410 Patients", Obesity Surgery (2005) pp. 1304-1308, vol. 15.

Soper, R., et al., "Gastric Bypass for Morbid Obesity in Children and Adolescents", Journal of Pediatric Surgery (Feb. 1975) pp. 51-58. vol. 10, No. 1.

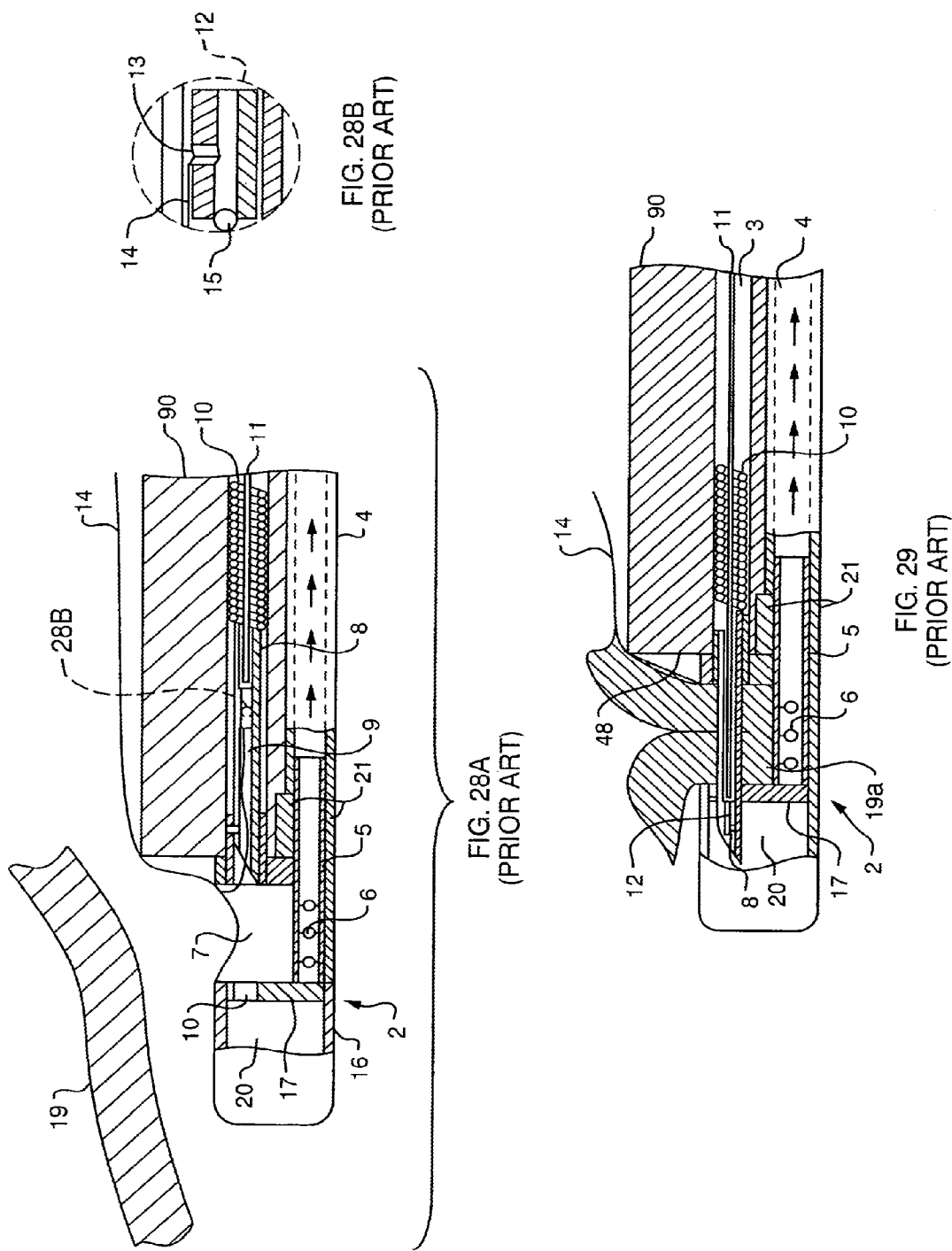

TISSUE CAPTURING AND SUTURING DEVICE AND METHOD

RELATED APPLICATIONS

This application is a continuation of U.S. application Ser. No. 12/070,673, filed on Feb. 20, 2008, now U.S. Pat. No. 8,388,632 which is a continuation of U.S. application Ser. No. 11/803,956, now U.S. Pat. No. 7,951,157 filed on May 16, 2007, which is a continuation of U.S. application Ser. No. 10/275,534, filed on Nov. 6, 2002, now U.S. Pat. No. 7,220,266 which is the U.S. National Stage of International Application No. PCT/US01/16025, filed on May 19, 2001, which claims the benefit of U.S. Provisional Application Nos. 60/205,444, filed on May 19, 2000, 60/205,741, filed on May 19, 2000, and 60/253,970, filed on Nov. 29, 2000, and International Application No. PCT/US01/07349, filed Mar. 5, 2001, the entire contents of which are incorporated herein by reference.

FIELD OF THE INVENTION

The present invention relates to a novel combination of endoscopic tissue apposition devices and suture clip delivery devices. Specifically, the invention provides an endoscopic apposition device configured to collect and secure a plurality of tissue portions with a single intubation of the device. The invention is applicable to both flexible and rigid endoscopy.

BACKGROUND OF THE INVENTION

Endoscopic apposition devices are devices that can be used in the body of a patient without the need to make an external incision in the patient, the device being controlled externally of the patient by endoscopic means. Apposition devices may comprise a sewing or stapling device for use in flexible endoscopy, though it is also applicable to devices for use in rigid endoscopy.

Endoscopic tissue apposition devices are useful to help perform a gastroplasty procedure to correct a condition known as gastro-esophageal reflux disease (GERD). This condition, believed to afflict as many as 15,000,000 individuals in the United States alone, results from the inability of the sphincter muscle (known as the lower esophageal or cardiac sphincter), at the junction between the stomach and the esophagus to function properly. Such malfunction enables reflux of stomach acid into the esophagus. The object of the gastroplasty procedure is to stitch together portions of stomach tissue into plications in a region proximal to the malfunctioning sphincter to reduce the cross-sectional area of the gastro-esophageal juncture and mimic the valve-like function of the sphincter.

To perform the procedure, an apposition device, such as a sewing capsule is attached to the end of a viewing endoscope and is inserted through a patient's esophagus to form a plurality of stitches in stomach tissue slightly below the sphincter. The sewing capsule has an aspiration port for generating negative pressure to suction stomach wall tissue into the sewing capsule. A first stitch is made through the stomach tissue to one side of the esophagus, and a second stitch is made, with the same suture thread, in stomach tissue adjacent to the first stitch. The two stitches then are drawn together to pull together the diametrically opposed, stitched stomach portions. In a preferred procedure, a tubular configuration having a somewhat figure-eight cross-sectional configuration is formed.

In accordance with what has been, until now, the conventional procedure followed, after the sutures are applied, the endoscope is removed from the patient and a knot is tied with the free ends of the suture thread that extend outside of the patient to maintain the figure-eight configuration. The knot is pushed down to the site of the sutures by a thread guide device that has been positioned at the distal end of the endoscope. To help navigate the knot to a location where it will effectively hold the tissue, the knot is viewed through the viewing channel of the endoscope as it is guided to the stomach. To be visible through the endoscope, the knot must be maintained in front of the viewing channel port at the distal face of the endoscope while positioning the thread guide device so as not to block the viewing channel.

The suturing and knotting procedure is repeated several times at longitudinally spaced intervals to create a plurality of figure-eight configurations extending longitudinally of the esophagus into the stomach. Suturing the stomach tissue in this manner essentially lengthens the esophageal passage and defines a structure having a valving action that is proven effective to prevent gastro-esophageal reflux. After a sufficient number of knots and sutures have been placed, a thread cutter, also operable through the endoscope, may be employed to cut the suture thread at points that are close to the tissue.

Endoscopic sewing devices are described in, for example, U.S. Pat. Nos. 5,080,663 and 5,792,153. Those patents disclose a sewing device for passing a thread through a tissue portion, which comprises a hollow needle movable between a first position in which it is out of the said tissue portion and a second position in which it passes through the said tissue portion, and a thread carrier adapted to be attached to the thread and being receivable within the hollow needle. The sewing device comprises a body, which defines a cavity within which the tissue portion can be held by means of suction, and the hollow needle is mounted for movement in the body between the first and second positions.

U.S. Pat. No. 5,792,153 discloses two suturing device embodiments: a single stitch sewing device and a multiple stitch sewing device. In the single stitch device, a thread carrier is transported by the needle through the tissue as the latter passes from its first position to its second position. When the needle returns to its first position, the thread carrier is left behind in the distal end of the sewing capsule. In the multiple stitch device, the same procedure occurs, but it is followed by a further step in which the hollow needle travels from its first position to its second position, picks up the thread carrier, and returns it. A second stitch may be formed during the next step. The whole sequence of steps is repeated as many times as may be required to form the desired number of stitches.

Similar advancements have been made with respect to the suture securing step that follows the stitching step. One such improvement is disclosed in U.S. Pat. No. 5,584,861 to Swain. The Swain patent discloses a suture clip and suture clip delivery device that is used in place of half hitch knots. The disclosed suture clip is a cylinder with a plug that can be releasably secured in the cylinder. The disclosed suture clip delivery device includes a tube, the distal end of which has a recess for receiving the suture clip. An axially movable stirrup is provided at the distal end that has the capacity to be moved from a first position that secures the suture clip to the tube and a second position that allows for the suture clip to be removed from the recess.

An aperture is provided in the cylinder to receive the suture. The cylinder is advanced over the suture that exits from a proximal end of the cylinder and enters the tube. An aperture in a sidewall of the tube provides egress for the suture. The plug is then advanced down the tube and into the cylinder. The interfacing walls of the cylinder and plug capture the suture. A pusher is used to force the plug into the cylinder while the stirrup maintains the suture clip in the recess. Following plug insertion, the stirrup, which is offset from the center axis of the tube, is advanced distally from the distal end of the tube to release the suture clip from the tube.

With all the improvements provided by the sewing capsules and suture securing devices, significant problems persist with the described gastroplasty procedure. One of the significant problems is the time and number of intubations needed to perform the various procedural steps endoscopically. Due to a number of concerns, a patient is typically anesthetized for no more than approximately 40 minutes. In this period of time, procedures such as the gastroplasty procedure must be performed to completion.

Minimizing the number of intubations and reducing the procedure time during which the patient must be kept under conscious sedation are significant considerations in any endoscopic procedure. In the gastroplasty procedure, several intubations have to be performed to create several plications. The prior art suturing devices must be withdrawn from the patient for each successive stitch made with single-stitch embodiments and must otherwise be repositioned for each stitch made with multi-stitch embodiments. The same is true of the suture securing devices. The devices must be withdrawn and repositioned between successive suture securing steps. The use of such devices is invariably long and cumbersome. There is a need to provide an endoscopic tissue apposition device and suture securing device that minimizes procedure time and the number of intubations while still joining the same number of tissue plications together during the procedure.

To reduce the trauma experienced by a patient having multiple devices intubated numerous times for one gastroplasty procedure, an overtube is placed in the gastro-esophageal tract. Although an overtube provides a barrier between the devices used to perform the procedure and the luminal walls of the tract, the act of inserting the relatively large diameter tube into the tract and the presence of the tube in the tract are perhaps the most significant sources of patient discomfort. There is a need to eliminate the requirement for an overtube to perform the described gastroplasty procedure. The invention disclosed herein provides such an improvement.

It is among the general objects of the invention to provide a tissue apposition device and suture securing device that, in combination, eliminate the need to use an overtube when performing a gastroplasty procedure. A further object is to provide a tissue apposition device that is adapted to receive a secure securing device to eliminate the need for multiple intubations to secure a plurality of tissue plications required to attach or repair internal tissue by a tissue securement mechanism comprising suture or staples. It is another object of the invention to provide an endoscopic apposition device that is simple and economical to fabricate by injection molding techniques. It is another object of the invention to provide a tissue apposition device having longitudinal flexibility to be easily navigable through a natural body lumen while mounted at the distal end of an endoscope. It is another object of the invention to provide a simplified tissue suture means having an anchor at one end which can remain on the through side of tissue during the process of tissue securement. These and other objects of the invention will become apparent from a reading of the following sections.

It is to be appreciated that the combination tissue apposition and suture securing device disclosed herein has a potentially wide range of applications including, but not limited to, the attachment of devices, e.g., a pH monitor to the gastrointestinal wall, the closure of perforations or ulcers, the creation of anastomoses, plication formation to address severe obesity and polyp plications. The device can be used with an endoscope, can be formed as the terminus of a catheter in combination with a visualization device such as an fiberoptic eye wire as is known in the art.

SUMMARY OF THE INVENTION

The present invention pertains to improvements to endoscopic apposition device and suture clip delivery devices. The improvements may be embodied in a tissue apposition device similar to those disclosed in U.S. Pat. No. 5,792,153 or 5,080,663, or a stapling device such as is disclosed in U.S. Pat. No. 5,037,021. The disclosures of the above listed patents are incorporated by reference herein, in their entirety. The prior art endoscopic tissue apposition devices provided a mechanism for capturing only a single fold with one intubation. The present invention provides a tissue apposition device capable of capturing multiple tissue folds and securing the sutures used to capture the folds with one intubation. The elimination of the need for multiple intubations eliminates the need for an overtube with respect to endoscopic procedures performed in the gastro-esophageal tract.

The device is comprised of a generally cylindrically shaped capsule attachable to the distal end of an endoscope, preferably a flexible viewing endoscope. The capsule comprises, in one embodiment, a body having an arc shaped suction port into which can be captured portions of tissue. The suction port defines an opening to a vacuum chamber. The vacuum chamber is operated through a vacuum source line that can extend interiorly or exteriorly to the endoscope.

Application of vacuum pressure causes tissue to be suctioned into the suction port and into the vacuum where a needle assembly comprising a needle releasably locked to a pusher via mating surfaces and an outer locking sleeve is adapted to carry a suture in a distal axial direction through into and through the tissue and into a distal tip of the capsule. Formed in the distal tip of the capsule is a cavity adapted to receive the needle assembly. A pair of springs are oriented parallel in the cavity for receiving the needle assembly. Distal faces of the springs engage a proximal edge of the needle and provide a restraining force to retraction of the needle. The locking sleeve is proximally retracted which allows the pusher to disengage from the needle that remains restrained by the springs. The pusher is retracted to allow for the release of the sutured tissue fold.

Following release of the tissue fold, the pusher is re-advanced into the distal tip of the capsule. The locking sleeve is also advanced to lock the needle onto the pusher. Proximal retraction of the pusher in a locked condition with the needle overcomes the restraining force of the springs that flex radially outwardly to allow the needle to be retracted into the proximal end of the capsule. The needle assembly is now in a condition to implant a suture in a second tissue fold. The process can be continually repeated for virtually any selected number of tissue folds, all of which will be connected by a single suture, all with a single intubation.

The tissue apposition device of the present invention offers another advantage over previous designs in that the entire capsule body may be injection molded from a polymer material. A single piece injection molded unit is easier to produce than previous capsule designs, which were machined from metal and comprise several assembled components.

In another aspect of the invention, the tissue apposition capsule body is adapted to utilize and receive a novel tissue suturing device. One tissue securement mechanism embodiment comprises sutures having anchoring elements at one end that permit them to be passed through tissue and then become anchored behind the tissue layer to permit suturing and retention of the fold of tissue. The anchoring element of the special suture material, such as polypropylene, may comprise a cylindrical tube with detents formed in a sidewall of the tube. A needle having a longitudinal slot and a channel is adapted to receive the anchor or tag and deposit it in the distal tip of the capsule. In this embodiment, the needle is retrieved with the pusher and the tag is retained in the capsule distal tip by virtue of the interaction of the detents with the springs. To allow release of the tag from the needle, the locking sleeve is only partially retracted to allow the distal end of the needle to expand radially outwardly while the proximal end is radially restrained to maintain engagement with the pusher. Following release of the sutured tissue fold, the needle/pusher assembly is reintroduced into the distal tip and the locking sleeve fully advanced to retrieve the tag. In an alternate embodiment, the tag is released with the sutured tissue fold and the needle is retracted out of the endoscope for the loading of another anchor for insertion into another tissue fold.

Also described herein is a suture clip delivery device adapted for navigation through the working channel of an endoscope and through the capsule channel adapted to receive the needle assembly. The delivery device comprises a multi-coaxial catheter with a three or four finger collet jaw affixed at a distal end. The catheter has a distal end from which the collet fingers distally project. The collet fingers are made of a material such as stainless steel or an engineering grade of plastic that allow the collet fingers to flex or spring from a pre-biased first open position to a second closed position and back to the first position. Alternatively, the collet fingers can be designed to flex or spring from a pre-biased first closed position to a second open position and back to the first position. The collet fingers define a cage within which a suture clip assembly is premounted. The cage is defined proximally by a distal end of the collet body and distally by flanges extending radially inwardly from the distal ends of the collet fingers. In one embodiment, the case is sized so that a plurality of suture clip plugs can be preloaded into the cage along with a single suture clip ring. By biasing the collet fingers in an open position, the need for cam surfaces and cam followers is eliminated.

In one embodiment, a separate control surface provided coaxially about the collet cage is employed to slide the outer sliding sleeve relative to the collet cage and the pusher. With any of the embodiments, the outer sliding sleeve is provided to secure the collet fingers in a closed position when placed in a distally advanced position. The outer sliding sleeve performs the additional function of severing the suture at a point proximal to the suture clip after engagement of the suture upon proximal retraction. One or more suture slots are provided in the distal end of the outer sliding sleeve to provide suture exits. A distal end of the suture slots can be sharpened to sever the suture. Upon proximal retraction of the outer sliding sleeve, the distal end of suture slot engages the suture and severs it when the distal end of the suture slot travels proximally to a cutting edge formed at or near the proximal end of the collet fingers. The design of the delivery device enables the suture clip to be cinched in close proximity to the sutured tissue as well as allow for the severing of the suture tails and release of the suture from the delivery device in one step.

The suture clips adapted for use with the suture clip delivery device are comprised of a plug and a ring that are configured to allow a suture to inter-wind through the clip in such a manner that the clips move with minimal friction while in an open position. The plug is a headless design that reduces abrasion of the suture as it exists the suture clip ends. In a closed position, the clip captures the suture by frictional engagement. The ring and plug components of the clip can be provided with interlocking features for enhancing the suture capturing effect.

Once threaded into the ring and plug, the suture is passed through finger slots formed between adjacent collet fingers and out the suture slot of the outer sliding sleeve. This enables the suture tails to be channeled externally of the catheter for removal at the proximal end of the catheter outside the patient after the tails have been severed at a point proximal to the now assembled suture clip. The catheter operator may thread a suture through a clip and then load the clip into the tooling or thread the suture through a premounted clip. After positioning the delivery system at the sutured tissue site, the device operator activates the handle to apply a distally directed force to the clip, thereby locking it to the suture. The application of force secures the clip components thus capturing the suture material within the mating surfaces. A second, proximally directed force is applied to the sliding sleeve to release radial restraint on the collet fingers that allows the secured suture clip to be deployed and to sever the suture tails in close proximity to the suture clip.

BRIEF DESCRIPTION OF DRAWINGS

The foregoing and other objects and advantages of the invention will be appreciated more fully from the following further description thereof, with reference to the accompanying drawings wherein:

FIGS. 28A-30 show successive steps in the operation of a prior art single stitch sewing device.

DETAILED DESCRIPTION OF THE PREFERRED EMBODIMENT

Figure 1:
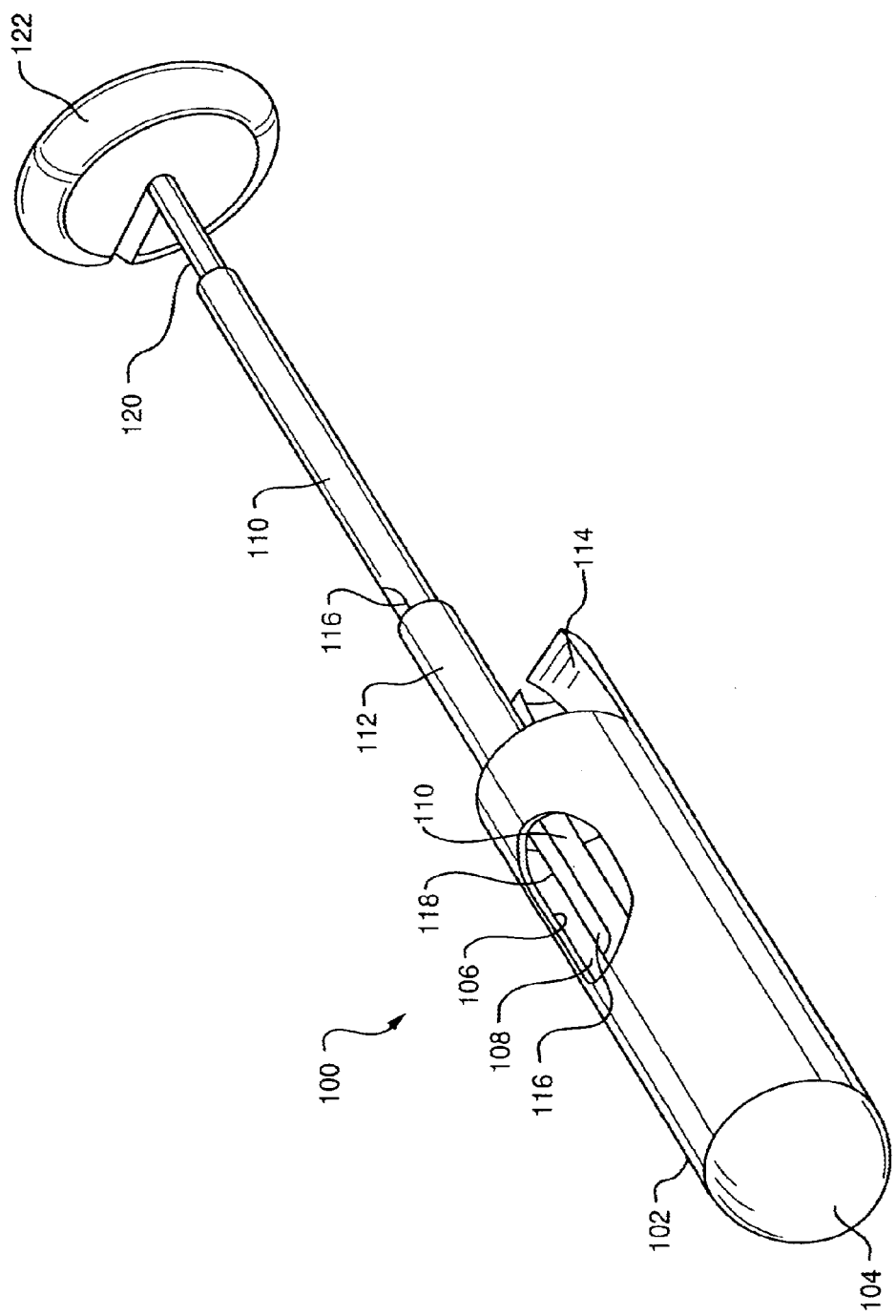
FIG. 1 is a perspective view of a suture capsule with a locking handle removed according to one embodiment of the invention.

A description of the embodiments of the present invention is best presented in conjunction with an explanation of the operation of a prior art tissue apposition device, which this invention serves to improve. FIGS. 28A-30 depict a prior art endoscopic suturing device disclosed in U.S. Pat. No. 5,792, 153. FIG. 28A shows the distal end of a flexible endoscope 90, on which a sewing device 2 is attached. The endoscope is provided with a viewing channel, which is not shown, but which terminates at a lens on the distal face of the endoscope. The endoscope is further provided with a biopsy or working channel 3, and a suction channel 4 the proximal end of which is connected to a source of vacuum (not shown). The suction channel 4 may comprise a separate tube that runs along the exterior of the endoscope, rather than an internal lumen as shown. The sewing device 2 has a tube 5, which communicates with the suction pipe 4 and has a plurality of perforations 6 therein. These perforations communicate with an upwardly open vacuum chamber 7 formed in the sewing device.

A hollow needle 8 is mounted in the biopsy channel 3, with its beveled tip extending into the sewing device. The needle has a channel 9 extending therethrough. A flexible, wire-wound cable 10 has its forward end attached to the rear of the needle 8, and a center wire 11 runs within the cable 10, along the entire length thereof, and is longitudinally movable with respect thereto. The diameter of the wire 11 is such that it is longitudinally movable within the channel 9 and, in the position shown in FIG. 28A, the forward end portion of the wire 11 extends into the rear end portion of the channel 9. A thread carrier in the form of a tag 12 is slidably and releasably mounted in the channel 9. The tag is shown in detail in FIG. 28B. The tag is hollow and has an aperture 13 extending through the sidewall thereof. As can also be seen in FIG. 1, one end of a thread 14 is secured to the tag by passing it through the aperture 13 and tying in the end of a knot 15 of sufficient size to prevent the thread escaping from the tag. The tag may be made from a relatively rigid material such as stainless steel.

At the distal end of the sewing device is defined a hollow head portion 16 defining a chamber 20 therein. Between the chamber 20 and the cavity 7 is a wall 17, in which an aperture 18 is formed. The aperture 18 has a diameter that is marginally greater than the external diameter of the needle 8, and is aligned therewith. The clearance between the needle 8 and the aperture 18 must be sufficiently small to prevent tissue being forced through the aperture and causing the needle to jam. Finally, FIG. 28A shows a portion of the patient's tissue 19, in which a stitch is to be formed.

In operation, suction is applied to the suction pipe 4, and thence, via the perforations 6 in the tube 5 to the cavity 7. This sucks into the cavity a U-shaped portion 19a of the tissue 19, as shown in FIG. 29. The hollow needle 8 is pushed through the U-shaped tissue portion 19a by extending distally the wire-wound cable 10 and associated needle 8. After full advancement of the needle through both folds of the U-shaped tissue portion, the tip potion of the needle 8 is distal to the wall 17 and within the chamber 20 in the hollow head portion 16. Distal movement of wire 11, slidably received within the wound cable 10, pushes the tag 12 out of the channel 9 and into the chamber 20 where it rotates out of alignment with aperture 18 to become captured in the chamber.

Figure 30:
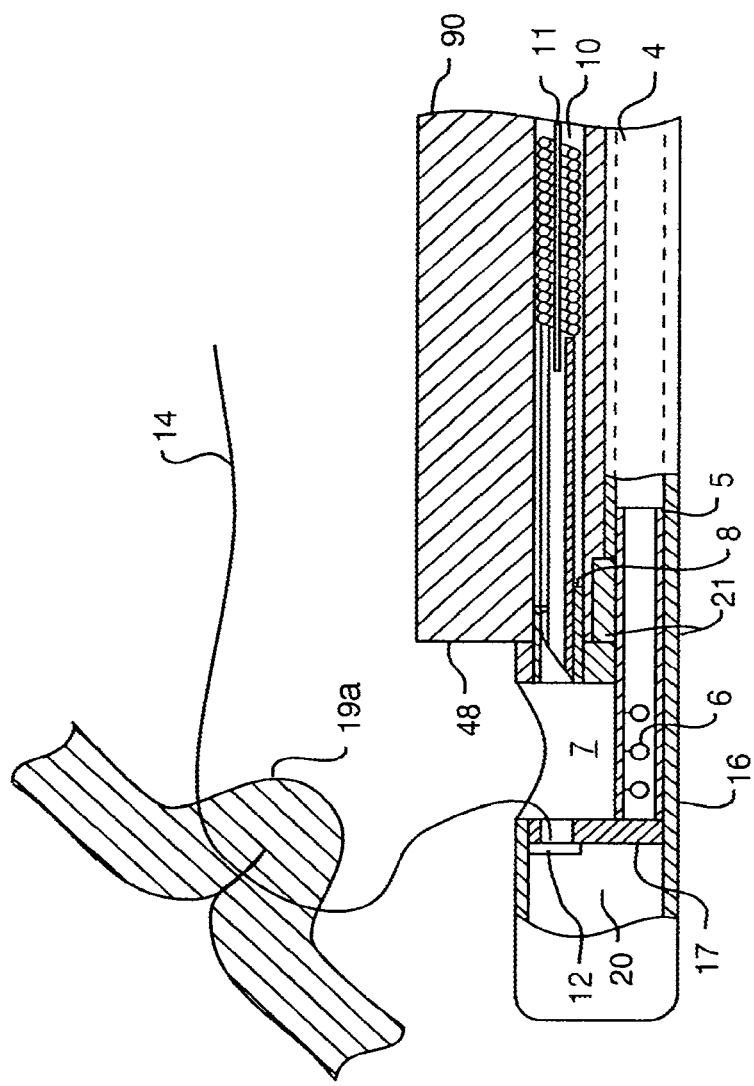

The wire 11 is then withdrawn proximally, followed by proximal withdrawal of the cable 10, to withdraw the needle 8 from the tissue portion 19a. The suction is then discontinued allowing the U-shaped tissue portion 19a to be released from the cavity 7. As shown in FIG. 30, the released tissue is left with a suture thread 14 passing through the two layers of tissue that form the U-shaped fold 19a. One end of the suture is joined to the tag 12 that remains captured in the chamber 20 and the other end of the suture extends through the patient's esophagus and out of the mouth. Finally, the endoscope and dewing device are withdrawn from the patient. In so doing, the thread 14 is pulled partially through the tissue portion 19a, as the captured tag 12 is withdrawn proximally and brought outside the patient.

With both ends of the thread 14 outside of the patient, the thread can be knotted and the knot endoscopically pushed down to the suture site and severed by an endoscopic knot pusher such as that disclosed in U.S. Pat. No. 6,010,515 (Swain et al). As an alternative to tying a knot, a suture lock or clip may be guided over the suture thread, down the esophagus and secured via an endoscope or suitable delivery catheter to hold the suture thread tight against the tissue. Examples of suitable suture locks and delivery systems are disclosed in PCT Application PCT/US01/filed Mar. 5, 2001, the contents of which are incorporated herein by reference. In using the endoscopic suturing device to treat G.E.R.D. it is believed that capture of multiple tissue portions and suturing and gathering them together provide an effective treatment. To accomplish this using the prior art device, multiple intubations of the endoscope down the patient's esophagus are required. Once, multiple (tissue portions, have been captured and sutured with thread, they are gathered together and secured by tying of surgical knots in the thread or application of suture lock devices. Each step in the process requires separate intubations which prompts the need for an overtube, which is known to cause significant patient discomfort. It is an object of the present invention to enable the capturing, suturing and securing of multiple tissue portions into multiple plications with one intubation and without the need for an overtube.

Figure 19:
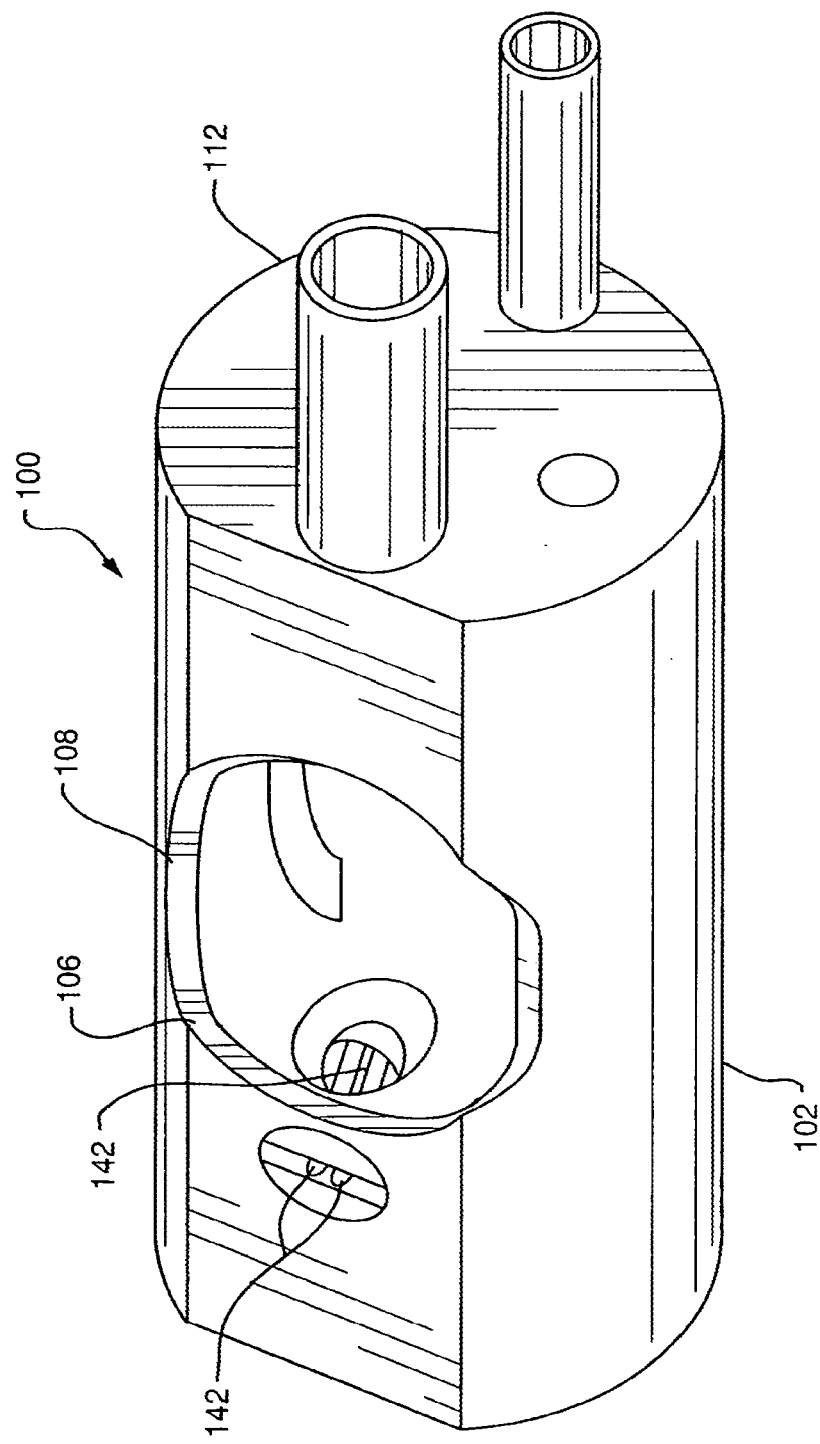
FIG. 19 is a somewhat diagrammatic view of a suture capsule according to one embodiment of the invention.
Figure 20:
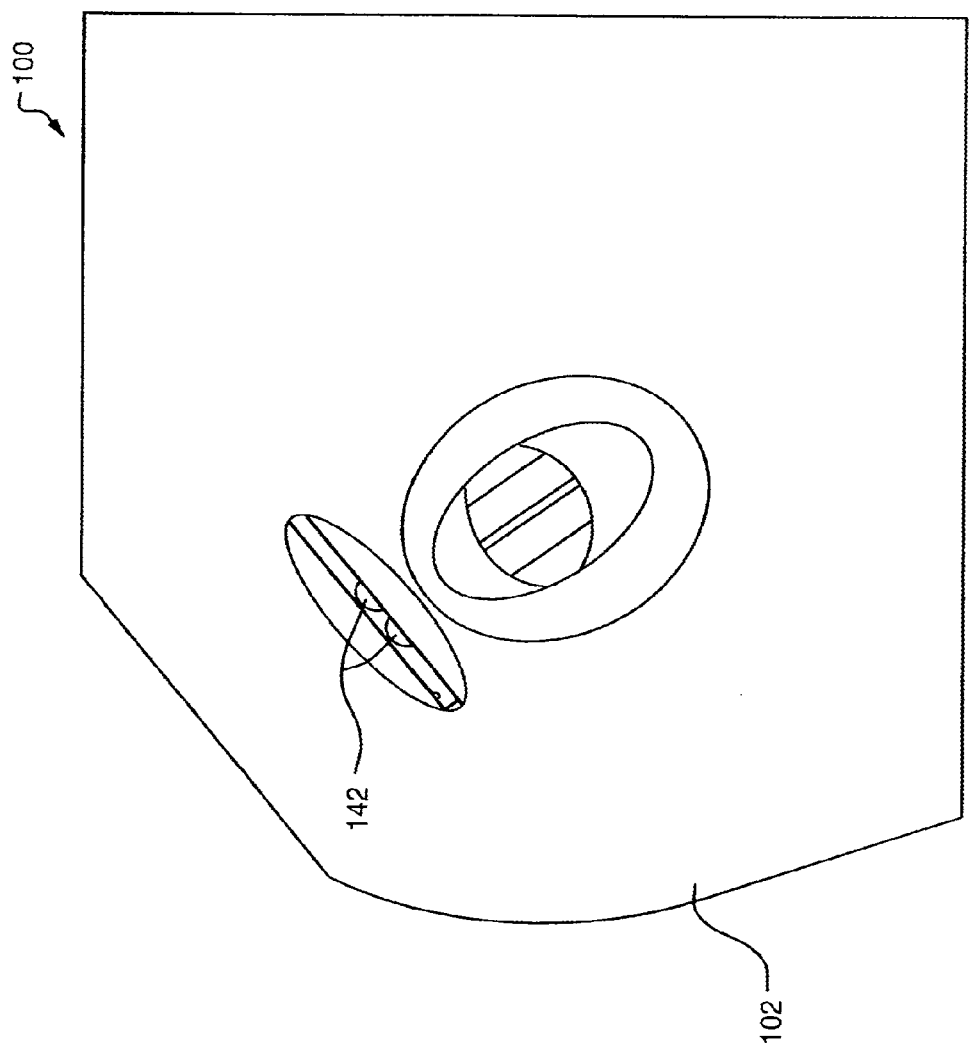
FIG. 20 is a partial sectional somewhat diagrammatic view of a suture capsule suction port and distal end according to one embodiment of the invention.

Referring to FIGS. 1, 19 and 20, a multi-functional sewing device designated generally as 100 is shown separate from an endoscope. The sewing device comprises a generally cylindrical capsule 102 made illustratively from a machined biocompatible metal such as stainless steel or from an injected molded engineering grade of plastic or polymer. Capsule 102 has a modular or integral distal tip 104 that is preferably hemispherical in configuration to enhance ease of advancement through luminal channels or cavities of a mammalian body and to minimize trauma and irritation to the contacted tissue surfaces. Distal tip 104 has portions defining a distal chamber (not shown) that is used to receive a needle or suture tag as described below. Proximal to the distal tip is a suction port 106 adapted to receive tissue suctioned into the port with vacuum pressure. Suction port 106 is preferably formed as an oval or circle to eliminate edges that could irritate suctioned tissue. Suction port 106 opens into a vacuum chamber 108 formed in the body of capsule 102 that is adapted to receive suctioned tissue in preparation for suturing.

A locking sleeve 110 (shown in suction port 106) extends through a channel (not shown) in the proximal end of capsule 102. A rigid attachment tube 112 integral to capsule 102 extends proximally from a proximal end of capsule 102 and is dimensioned to fit snugly within the working channel of an endoscope. Tube 112 provides leverage for securing capsule 102 to the distal end of an endoscope along with an attachment ramp 114 that uses a wedge (not shown) to frictionally engage and lock to the endoscope. A lumen of tube 112 is contiguous with the capsule channel through which locking sleeve 110 extends. Formed on a top surface of locking sleeve 110 is a flat surface 116 adapted to receive a suture 118. Surface 116 provides an essentially low friction abrasion-free passage for suture 118 proximal to its insertion into a needle 126 shown in FIG. 2. Surface 116 extends proximal to but not into a distal end of locking sleeve 110 to maintain concentricity and radial strength of the distal end.

A pusher 120 is provided to advance and retract needle 126. Pusher 120 is concentric to locking sleeve 110 and is dimensioned to extend through and slide freely within locking sleeve 110 as well as through and out the proximal end of the endoscope working channel to which capsule 102 is attached. Attached to a proximal end of pusher 120 is pusher handle 122 configured to provide a surface to apply hand pressure with the palm of a hand to advance needle 126 and a finger gripping surface on a distal side to retract needle 126.

Figure 2:
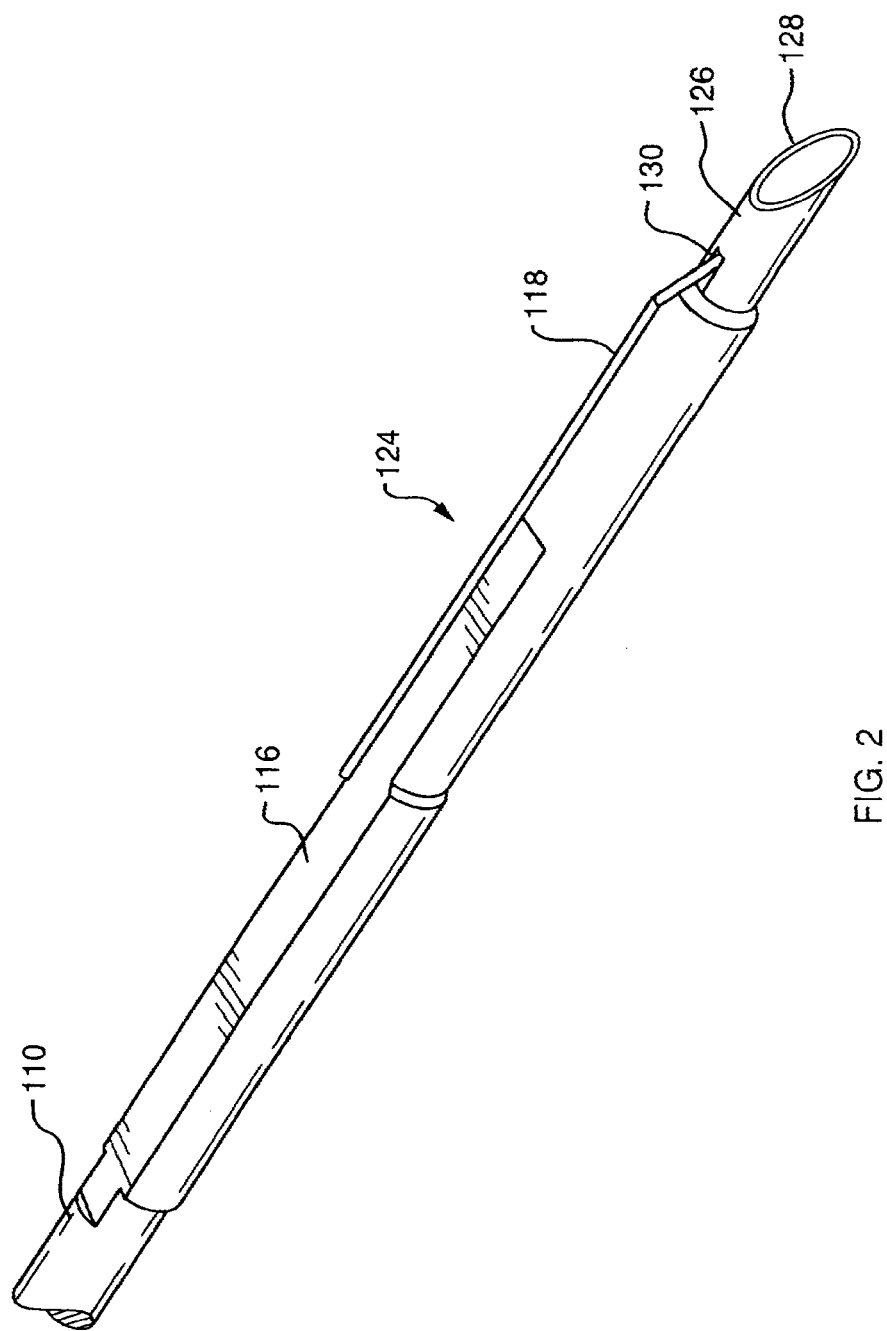
FIG. 2 is a perspective view of a needle assembly adapted for use in a suture capsule according to one embodiment of the invention.
Figure 3:
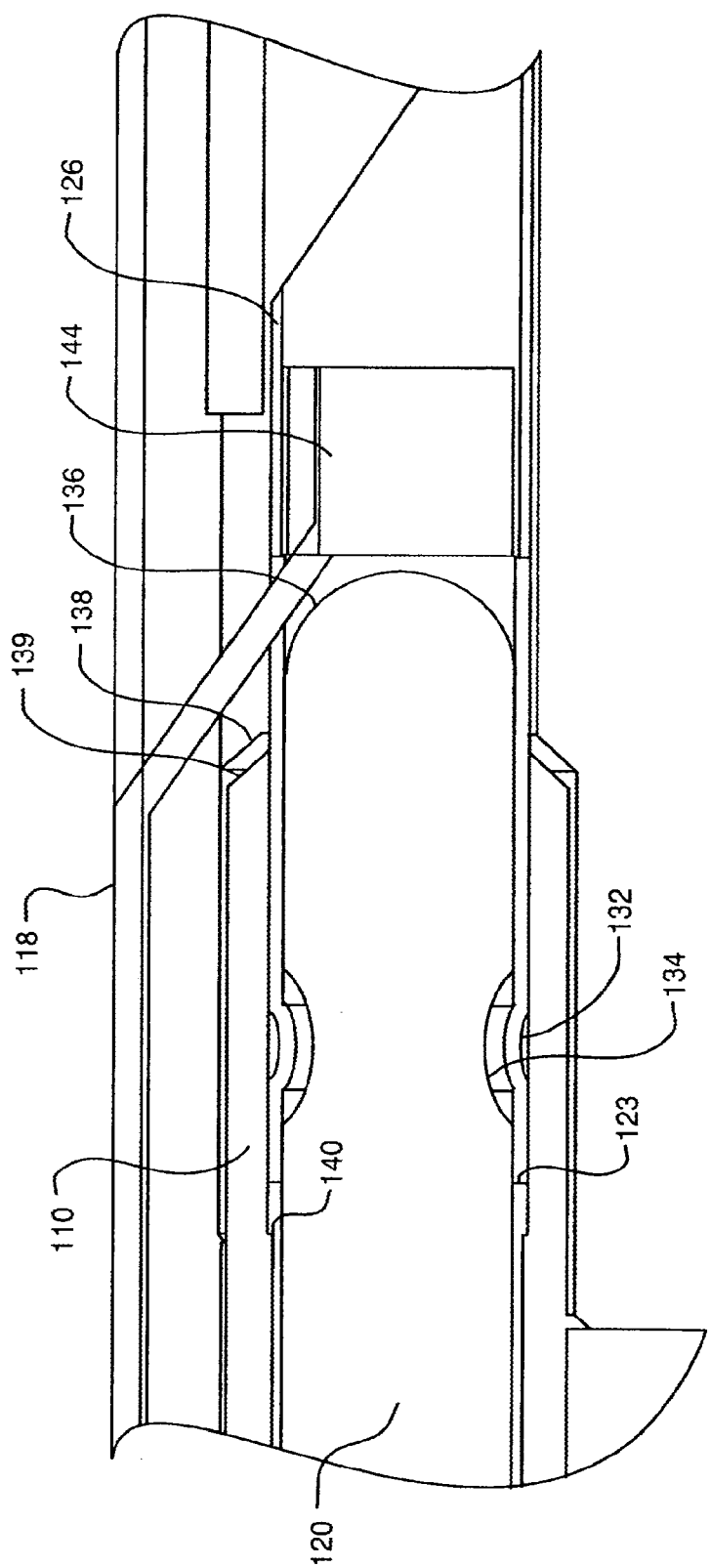
FIG. 3 is a partial sectional view of a capsule/locking sleeve/needle assembly according to one embodiment of the invention.
Figure 8:
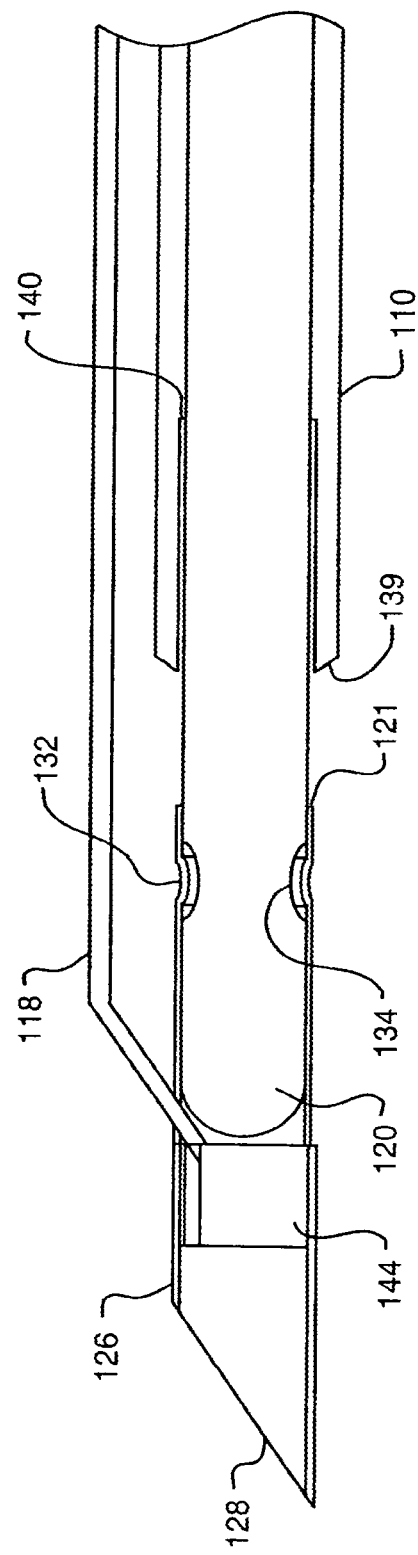
FIG. 8 is a partial sectional view of a needle assembly with a retracted locking sleeve according to one embodiment of the invention.
Figure 9:
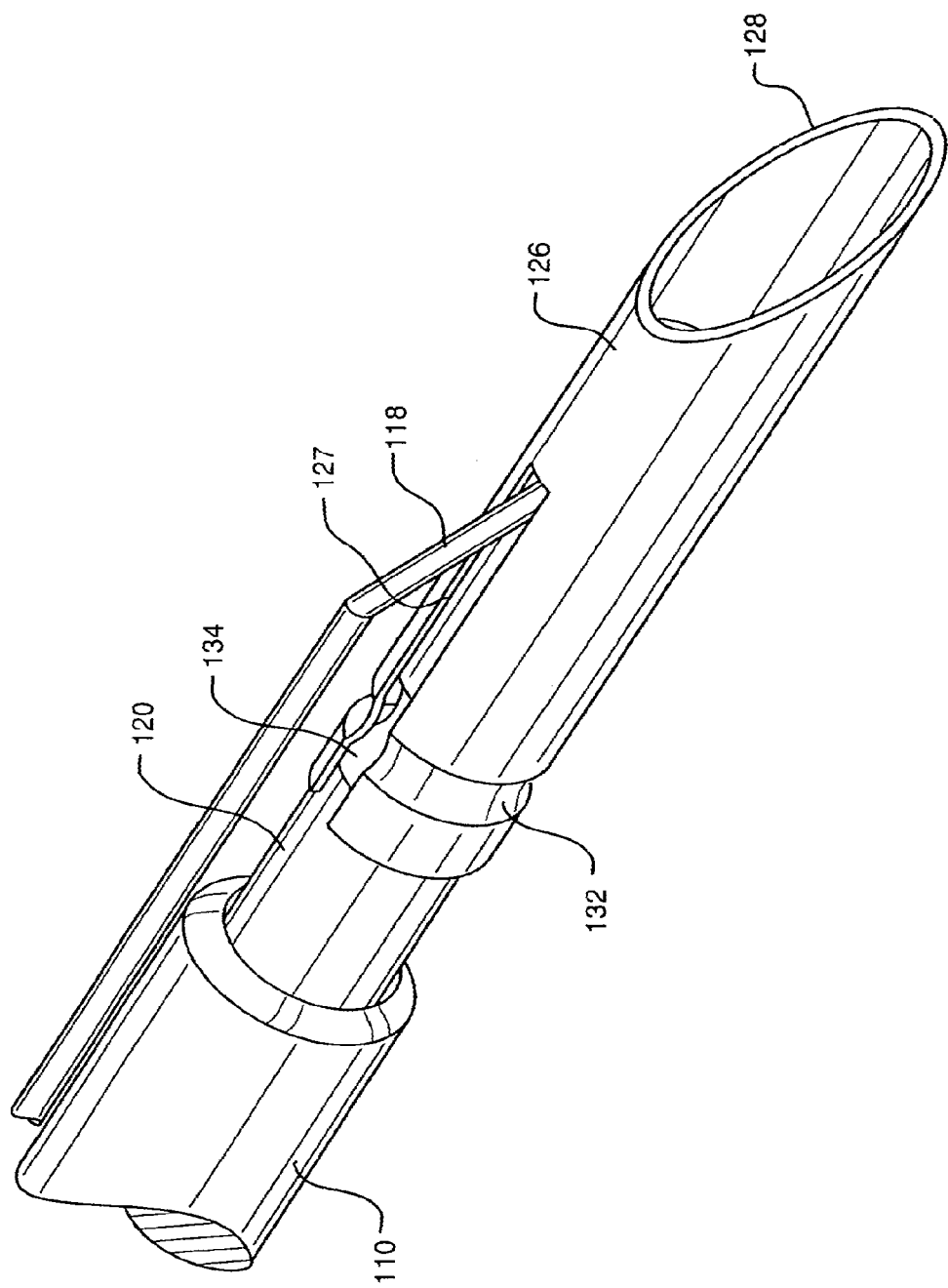
FIG. 9 is a top perspective view of the distal end of a needle assembly with a retracted locking sleeve according to one embodiment of the invention.
Figure 10A:
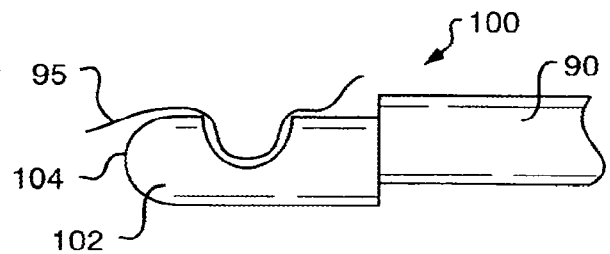
FIG. 10A is a partial side elevational view of a suture capsule/endoscope assembly with tissue suctioned into the suction port/vacuum chamber according to one embodiment of the invention.
Figure 10B:
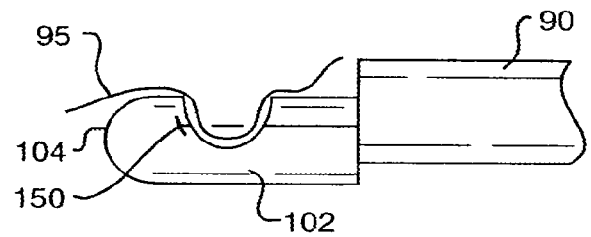
FIG. 10B is a partial side elevational view of a suture capsule/endoscope assembly with tissue suctioned into the suction port/vacuum chamber with a suture/tag assembly piercing the tissue according to one embodiment of the invention.
Figure 10C:
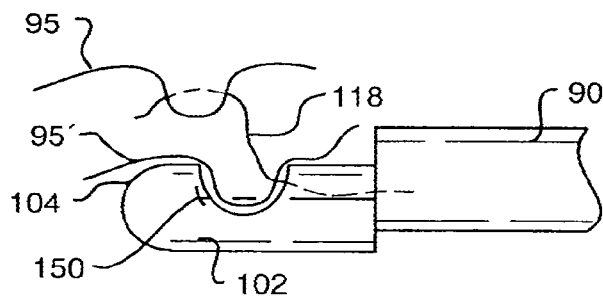
FIG. 10C is a partial side elevational view of a suture capsule/endoscope assembly with a released first tissue mound with embedded suture and distal anchor tag and a second tissue mound suctioned into the suction port/vacuum chamber with a suture/tag assembly piercing the second tissue mound according to one embodiment of the invention.
Figure 10D:
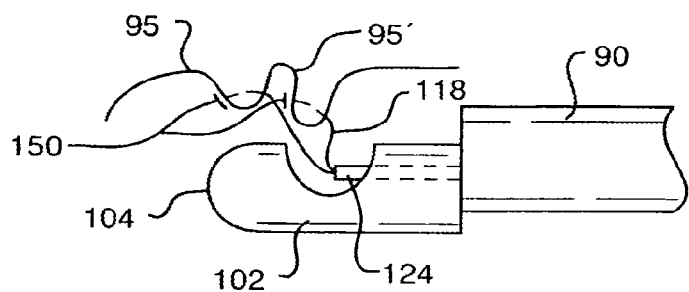
FIG. 10D is a partial side elevational view of a suture capsule/endoscope assembly with released first and second tissue mounds with a single suture embedded in each tissue mound with separate distal anchor tags.

Shown in FIGS. 2, 8 and 9 is a needle assembly designated generally as 124 that is comprised of the locking sleeve 110 and a slotted hypodermic needle 126 with a preferred beveled distal tip 128. Needle 126 can be made from any suitable biocompatible metal such as stainless steel or polymeric compound such as PEEK (polyetheretherketone), commercially available from Victrex. The compound is a linear aromatic semi-crystalline polymer. A needle suture slot 130 is formed preferably in a central portion of needle 126 to receive in locking engagement suture 118. Any number of methods can be used to secure suture 118 to needle 126 including crimping, staking, thermo bonding or melting (for needles made from polymeric materials), and knotting. FIGS. 3-8 show a suture locking plug 144 securing suture 118 to needle 126.

Shown in FIGS. 3-7 is needle 126 releasably locked to pusher 120 through the interaction of mating surfaces formed on the two components. Needle 126 has an inwardly directed annular ring 132 projecting from an inner wall of needle 126. Pusher 120 has an annular channel 134 dimensioned to conform to the shape of annular ring 132. Pusher 120 has a cross-sectional diameter that is dimensioned to fit within the inner diameter of needle 126. A distal tip of pusher 120 is preferably hemispherical in configuration to facilitate registration of pusher 120 in the proximal end of needle 126. Forward advancement of pusher 120 causes annular channel 134 to engage annular ring 132. Subsequent forward advancement of locking sleeve 110 secures the engagement of channel 134 to ring 132. In an alternative embodiment, the proximal portion of ring 132 is removed (not shown) so that the proximal end of needle 126 has a reduced neck configuration. This configuration eases the release of pusher 120 when retracted out of distal tip 104 subsequent to the retraction of locking sleeve 110.

Slots 127 formed in the annular wall of needle 120 extend from the proximal end toward the distal end, a fraction of the longitudinal length of needle 126. The slots are preferably diametrically opposed 180° and allow for the proximal end of needle 126 to flex radially outwardly. One or more slots can be used; two are preferred. The relative flexibility of the proximal end of needle 126 allows the portion of pusher 120 distal to channel 134 to traverse ring 132 during distal advancement. A sleeve channel 136 formed in the distal end of capsule 102, and concentric with the channel receiving needle 126, is dimensioned to receive in sliding engagement, locking sleeve 110. A distal end 138 of sleeve channel 136 is preferably beveled to the same degree as the distal end 139 of locking sleeve 110. Distal end 138 acts as a stop to prevent needle 126 from being advanced into the inner surface of distal tip 104. A shoulder 140 is formed on the inner surface of locking sleeve 110 for contacting a proximal edge 123 of needle 126 to maintain the concentricity of needle 126 when being urged distally in capsule 102.

Provided in distal tip 102 are detent springs 142, the distal edges of which contact the proximal edge 121 of needle 120. Springs 142 are preferably substantially parallel and oriented perpendicular to the capsule longitudinal axis. The ends of the springs 142 are secured to the inner wall of distal tip 102 by either sitting in annular depressions formed on the inner wall or by mechanical fasteners. Springs 142 are adapted to provide a mechanical stop that prevents needle 126 from being retracted out of distal tip 104 when pusher 120 is retracted. To perform this retention function, any spring can be used that can apply a radial force to needle. Among the possible variants are flat, round and helical springs. The importance of this function is explained below.

Figure 12:
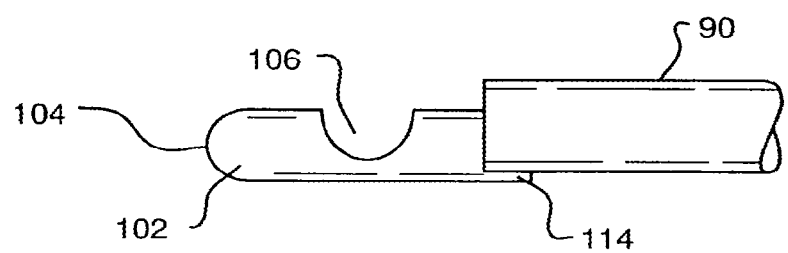
FIG. 12 is a schematic view of a suture capsule/endoscope assembly according to one embodiment of the invention.
Figure 18A:
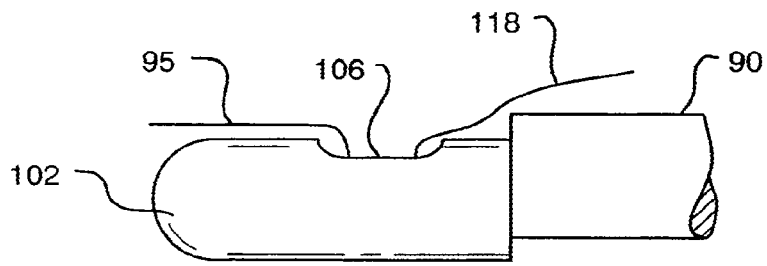
FIG. 18A is a side elevational view of a suture capsule/endoscope assembly with tissue suctioned into the suction port and vacuum chamber according to one embodiment of the invention.
Figure 18B:
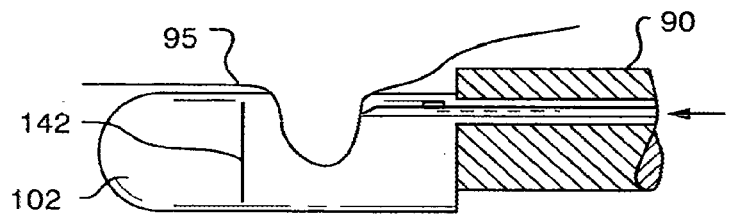
FIG. 18B is a side elevational view of a suture capsule/endoscope assembly with tissue suctioned into a suction port and vacuum chamber and with a needle assembly advanced to a proximal end of the tissue according to one embodiment of the invention.
Figure 18C:
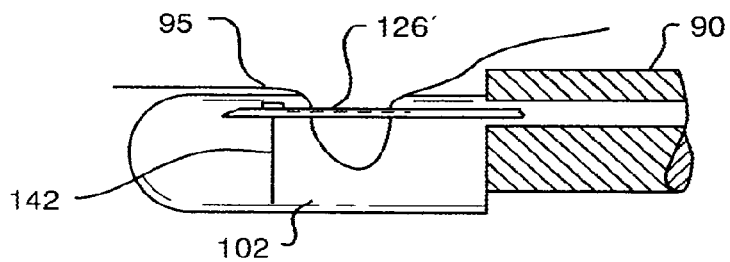
FIG. 18C is a side elevational view of a suture capsule/endoscope assembly with a needle/suture/tag assembly advanced distally through the tissue according to one embodiment of the invention.
Figure 18D:
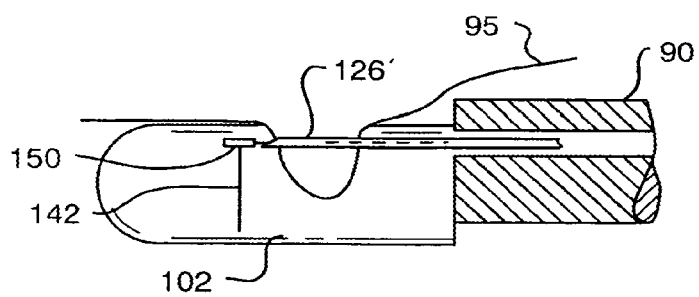
FIG. 18D is a side elevational view of a suture capsule/endoscope assembly with a partially retracted needle and a suture tag assembly releasably locked into a distal end of the suture capsule according to one embodiment of the invention.
Figure 18E:
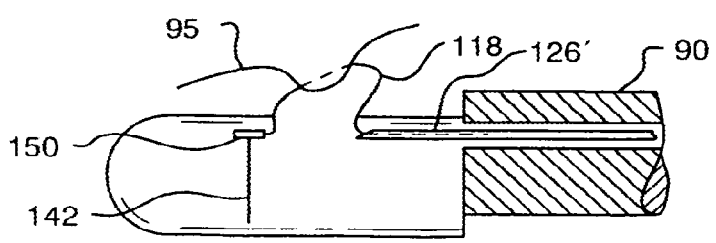
FIG. 18E is a side elevational view of a suture capsule/endoscope assembly with a fully retracted needle and a released tissue mound pierced by a suture.
Figure 18F:
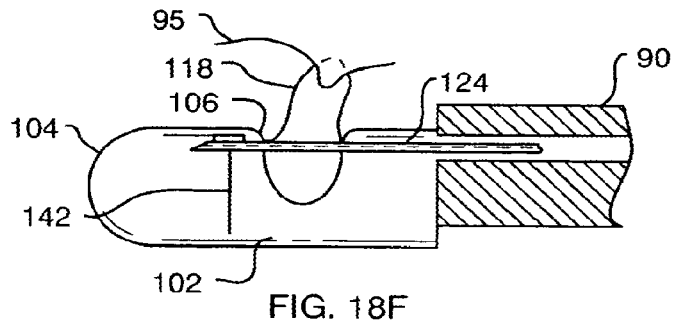
FIG. 18F is a side elevational view of a suture capsule/endoscope assembly with a released tissue mound pierced by a suture and a distally advanced needle encompassing a suture anchoring tag according to one embodiment of the invention.
Figure 18G:
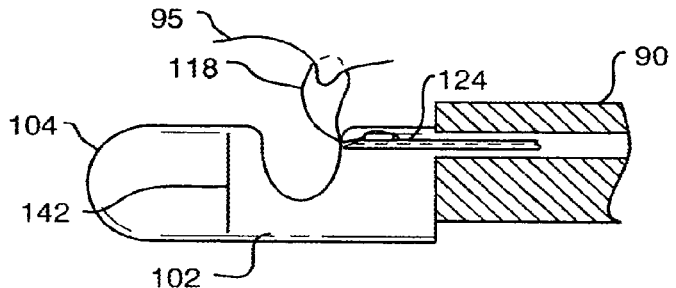
FIG. 18G is a side elevational view of a suture capsule/endoscope assembly with a released tissue mound and a retracted needle/tag assembly according to one embodiment of the invention.
Figure 18H:
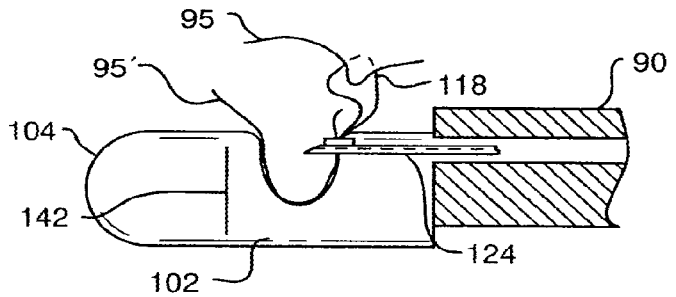
FIG. 18H is a side elevational view of a suture capsule/endoscope assembly with a released tissue mound pierced by a suture and a second tissue mound suctioned into a suction port and vacuum chamber with a needle/tag assembly partially piercing the second mound according to one embodiment of the invention.
Figure 18I:
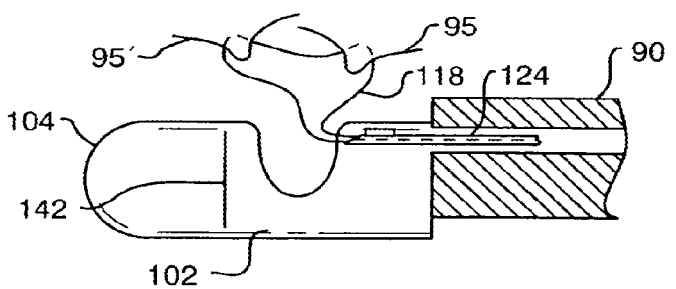
FIG. 18I is a side elevational view of a suture capsule/endoscope assembly with two released tissue mounds pierced by a suture with a needle/tag assembly in a retracted position according to one embodiment of the invention.
Figure 18J:
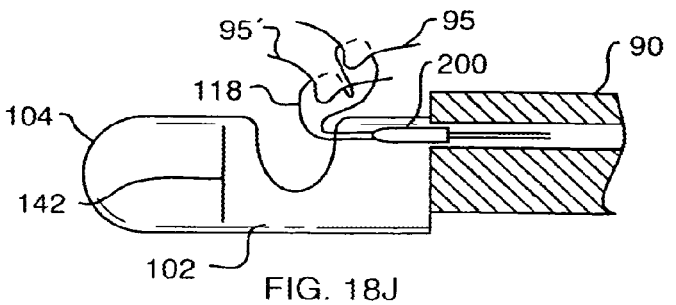
FIG. 18J is a side elevational view of a suture capsule/endoscope assembly with two released tissue mounds pierced by a suture with a suture clip delivery device partially advanced in the suture capsule according to one embodiment of the invention.
Figure 18K:
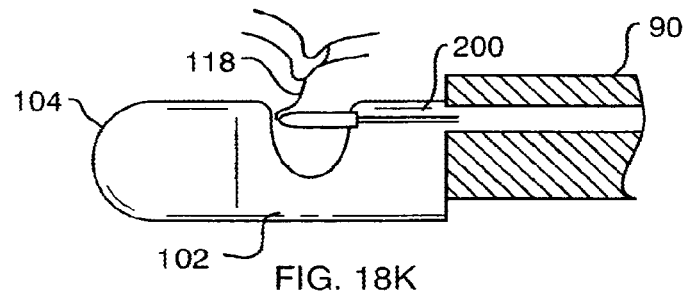
FIG. 18K is a side elevational view of a suture capsule/endoscope assembly with two released tissue mounds pierced by a suture with a suture clip delivery device fully advanced in the suture capsule in a pre-cinched state according to one embodiment of the invention.
Figure 18L:
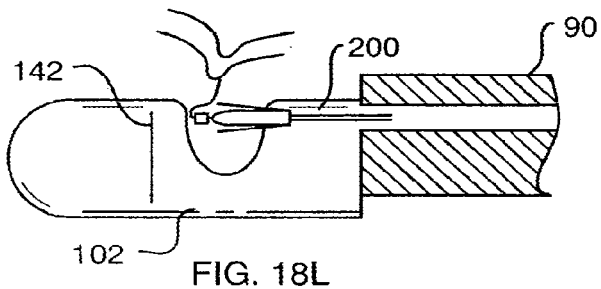
FIG. 18L is a side elevational view of a suture capsule/endoscope assembly with two released tissue mounds pierced by a suture and cinched with a suture clip secured to the suture and being deployed by a suture clip delivery device according to one embodiment of the invention.
Figure 18M:
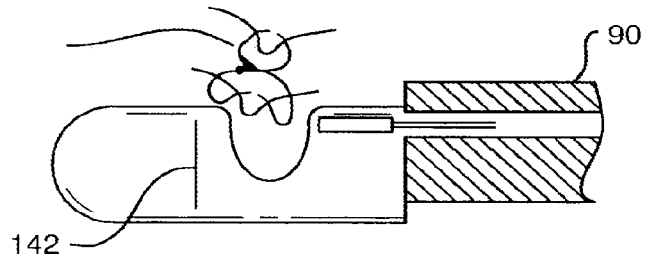
FIG. 18M is a side elevational view of a suture capsule/endoscope assembly with a cinched plication and a partially retracted suture clip delivery device according to one embodiment of the invention.
Figure 18N:
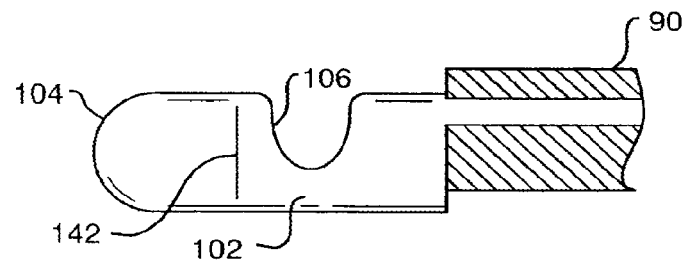
FIG. 18N is a side elevational view of a suture capsule/endoscope assembly with a tag retention detent in the capsule distal end according to one embodiment of the invention.
Figure 18O:
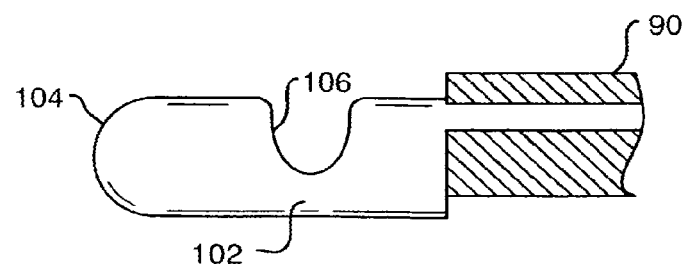
FIG. 18O is a side elevational view of a suture capsule/endoscope assembly without a tag retention detent in the capsule distal end according to one embodiment of the invention.

To operate this embodiment of the invention, sewing device 100 is back-loaded into the working channel of an endoscope 90 and secured to its distal end as shown in FIGS. 12, 18N and 18O. A suture 118 is secured to needle 124 after being threaded through the working channel of the endoscope and over flat surface 116 of locking sleeve 110. The endoscope/sewing device assembly is advanced through a body lumen to a selected site, preferably within the stomach below the lower esophageal or cardiac sphincter. Once in place, vacuum pressure is commenced in vacuum chamber 108 from a source external to the endoscope to suction tissue from the body lumen into suction port 106. Needle 126 with attached suture 118 is advanced distally through the tissue and into distal tip 104 of capsule 102. Distal advancement of needle 126 is accomplished by providing a distally directed force to pusher handle 122 that causes distal translation of pusher 120 and needle 126. Preferably, a locking sleeve handle (not shown), attached to the proximal end of locking sleeve 110 and located distal to pusher handle 122, projects proximally from the proximal end of the endoscope, and is advanced simultaneously with pusher handle 122 to ensure a positive lock between needle 126 and pusher 120. Locking sleeve 110 can be maintained in a distally extended position by maintaining manual pressure on the locking sleeve handle or via springs as described in PCT Application No. PCT/US01/07349.

Figure 4:
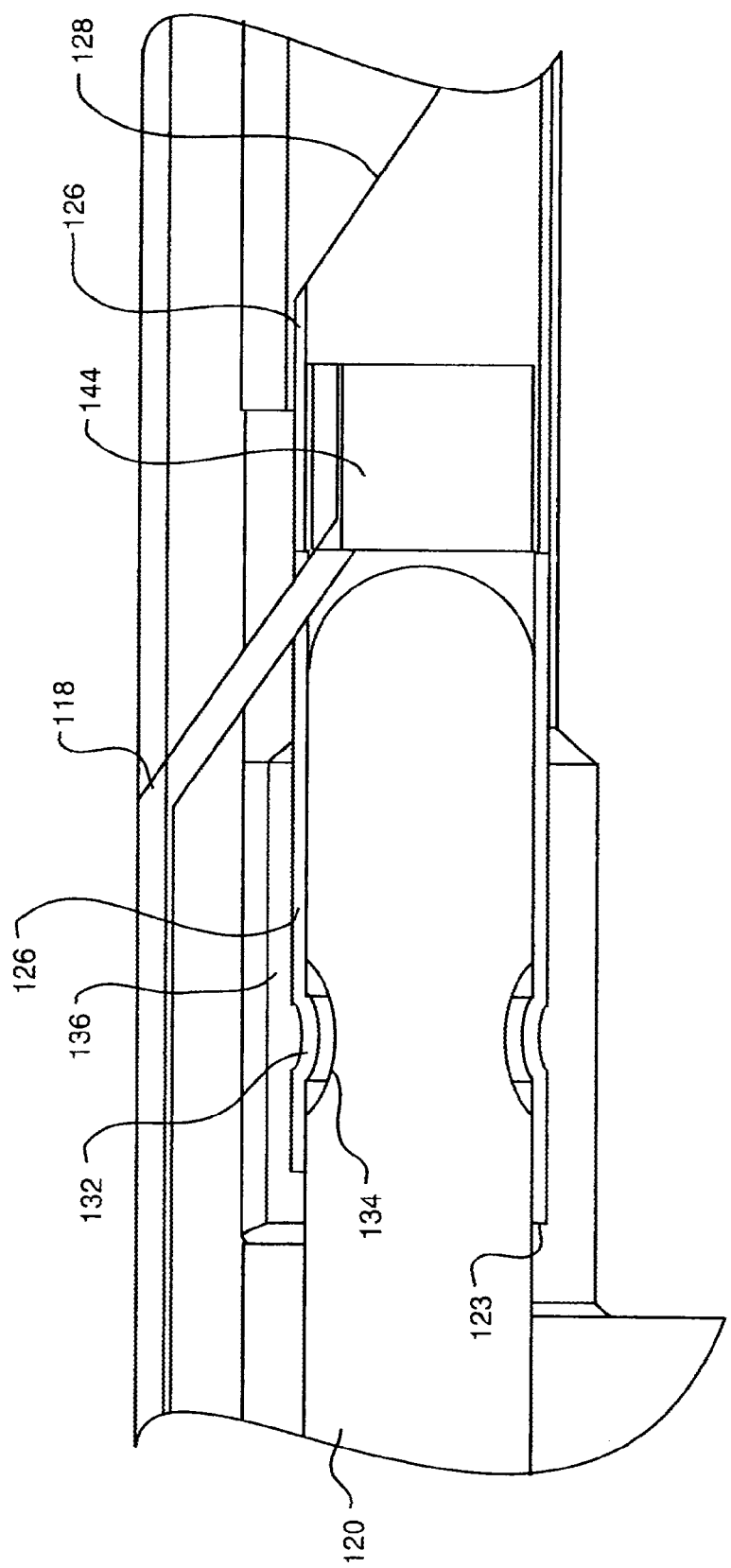
FIG. 4 is a partial sectional view of a capsule/needle assembly according to one embodiment of the invention.
Figure 5:
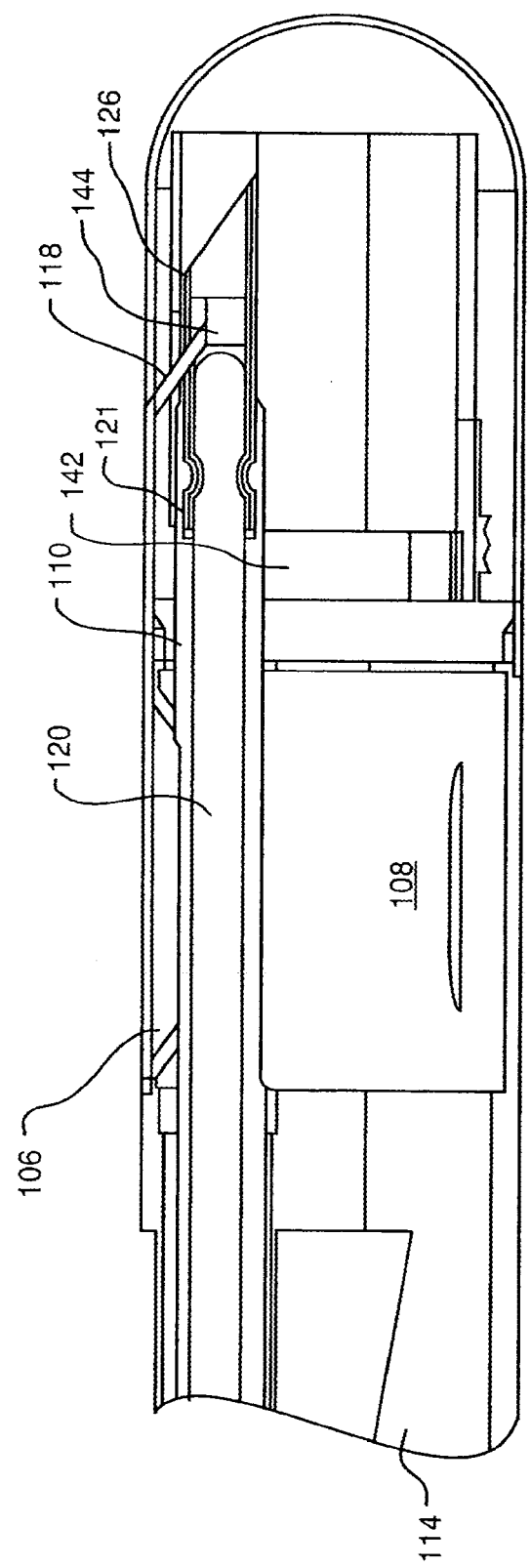
FIG. 5 is a partial sectional view of a capsule/locking sleeve/needle assembly according to another embodiment of the invention.
Figure 6:
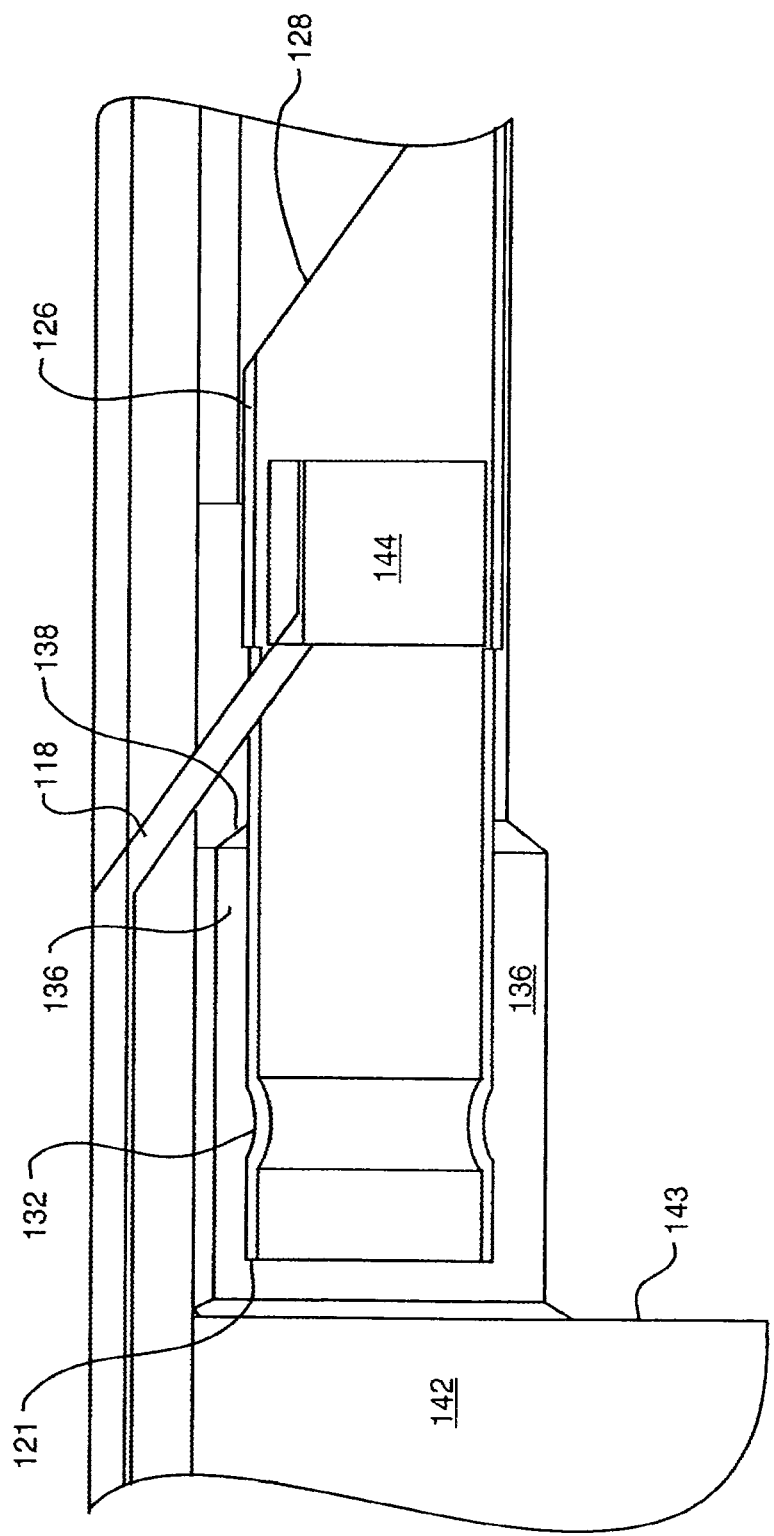
FIG. 6 is a partial sectional view of a needle assembly with a suture secured to the needle disengaged from a pusher in a distal end of a suture capsule according to one embodiment of the invention.
Figure 7:
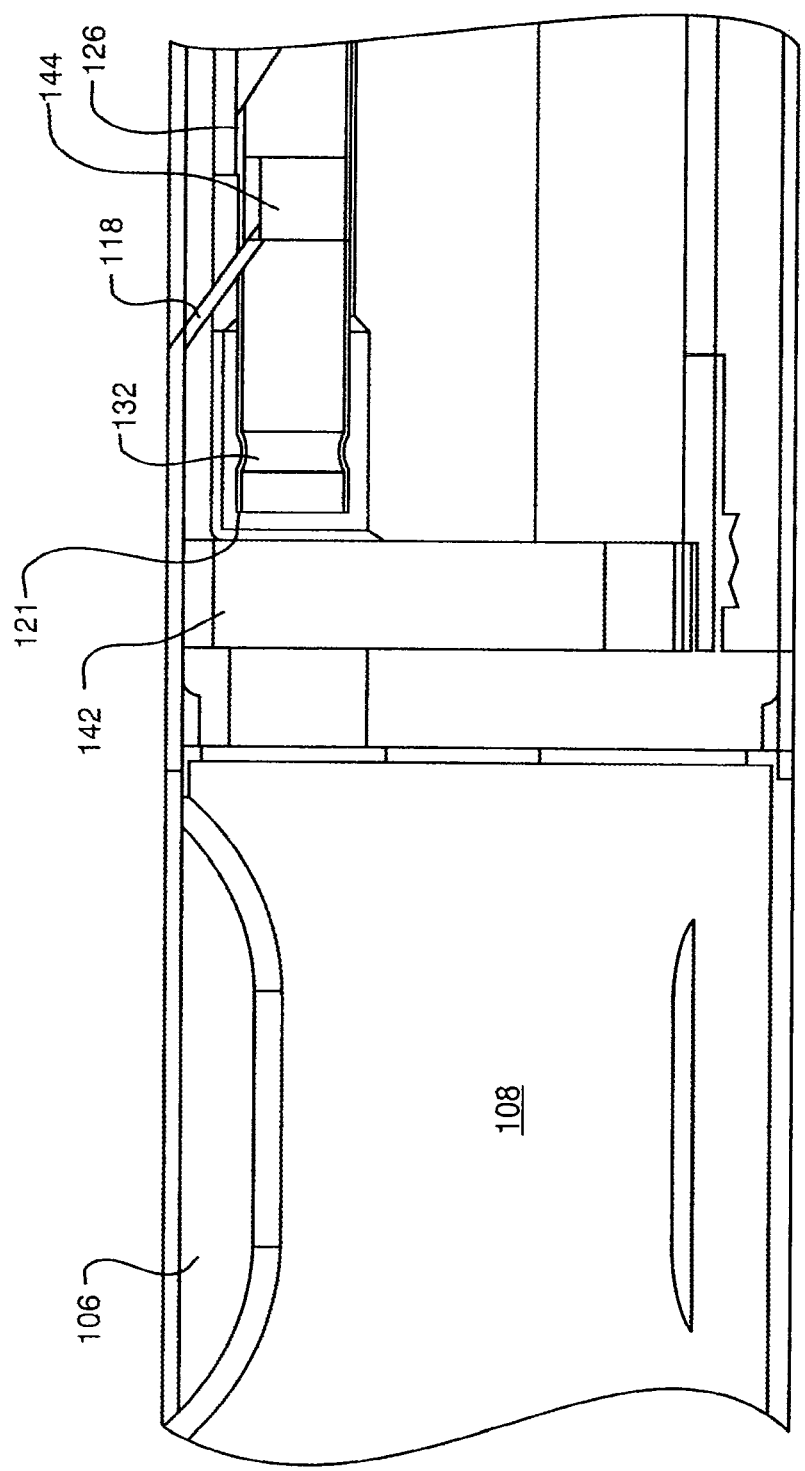
FIG. 7 is a partial sectional view of a suture capsule vacuum chamber and distal cavity with a needle assembly lodged in the distal cavity according to one embodiment of the invention.

Distal advancement of the pusher/locking sleeve/needle assembly is continued until distal end 139 of locking sleeve 110 contacts distal end 138 of locking channel 136. The distal travel of needle 126 into distal tip 104 results in the proximal end of needle 126 advancing distally past a distal edge 143 of springs 142 as illustrated in FIG. 6. With suture 118 advanced completely through the captured tissue, locking sleeve 110 is proximally retracted to allow for the disengagement of pusher 120 from needle 126 (FIG. 4). Preferably, locking sleeve 110 is retracted until distal end 139 is proximal to vacuum chamber 108.

Proximal retraction of pusher 120 while still engaged to needle 126 causes proximal edge 121 to register with distal edge 143 of spring 142 thereby restraining needle 126 in distal tip 104. Further retraction of pusher 120 coupled with the restraining force provided by spring 142 causes the proximal end of needle 126 to flex radially outwardly thereby disengaging the mating surfaces of ring 132 and channel 134. Needle 126 is cradled in distal tip 104 by the cylindrical opening formed in distal tip 104. To allow for the release of the captured tissue, pusher 120 is retracted proximal to vacuum chamber 108. Following retraction of locking sleeve 110 and pusher 120, the vacuum pressure is terminated which releases the captured tissue.

To prepare sewing device 100 to capture and suture another fold of tissue, pusher 120 is re-advanced through vacuum chamber 108, through springs 142 which expand radially outwardly and into the proximal end of needle 126. Locking sleeve 110 is advanced either simultaneously or slightly behind pusher 120 to lock the engagement of ring 132 and channel 134. With locking sleeve 110 maintained over pusher 120 and needle 126, pusher handle 122 and handle for locking sleeve 110 are proximally retracted as a unit to retract needle 126 out of distal tip 104. Needle assembly 124 is retracted until substantially proximal to vacuum chamber 108. The cycle is then repeated for a new portion of stomach wall tissue using the same needle and the same suture without the need for multiple intubations. Once the desired number of tissue mounds has been sutured, needle 126 is retracted out the proximal end of locking sleeve 110 to allow removal of needle 126 from the suture. The suture is then threaded into a suture securing device as described below. It is to be noted that the use of the same suture to secure multiple tissue folds allows for the determination of the distance between adjacent tissue folds. Suture 118 is typically provided on a reel having graduations. By monitoring the length of suture being advanced off the reel from one tissue fold to the next, the operator can approximate the distance of the tissue folds.

Figure 15A:
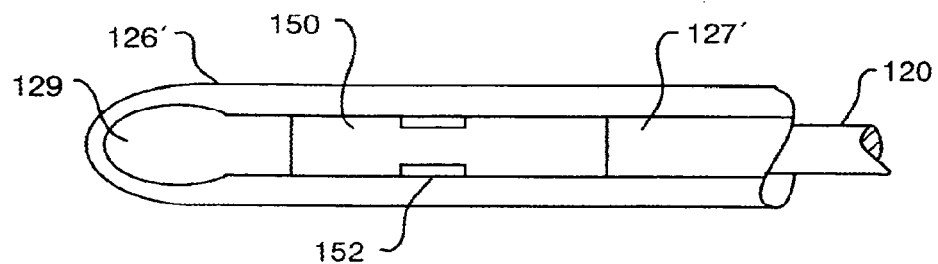
FIG. 15A is a top view of a needle/pusher assembly according to one embodiment of the invention.
Figure 15B:
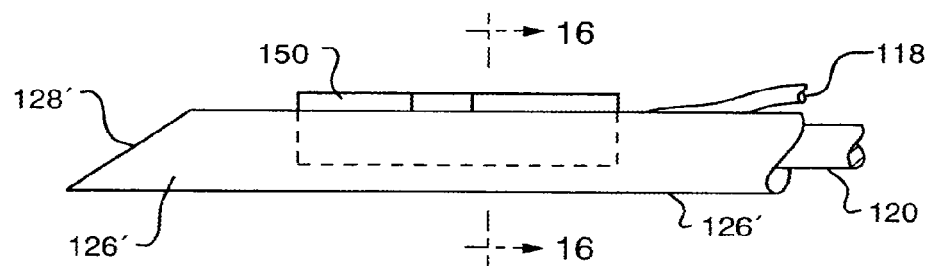
FIG. 15B is a side elevational view of the needle/pusher assembly shown in FIG. 15A.
Figure 16:
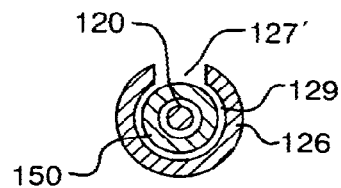
FIG. 16 is a sectional view of the needle/pusher assembly shown in FIGS. 15A and 15B.
Figure 17:
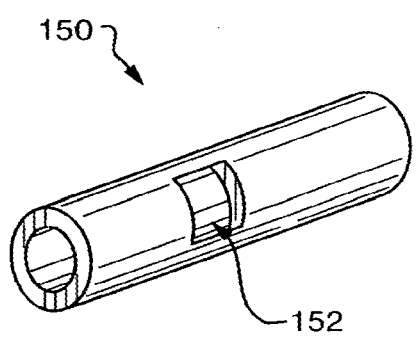
FIG. 17 is a perspective view of a needle assembly according to one embodiment of the invention.

In an alternative embodiment, a suture tag 150 is used in conjunction with needle 126 to effectuate the suturing of multiple tissue mounds with one intubation. Depicted in FIG. 17, tag 150 is a generally cylindrical in overall shape with a through bore formed preferably along a central longitudinal axis. Formed in a sidewall of tag 150 are notches 152 that are preferably diametrically opposed to engage springs 142. Tags 150 are dimensioned to fit within a channel 129 formed in a needle 126' that is a modified version of needle 126 as shown in FIGS. 15A, 15B and 16. The dimensions of tag 152 are adjusted so that a sidewall of tag 150 frictionally engages an inner wall of needle 126' when locking sleeve 110 is advanced distally over needle 120. The frictional engagement is sufficient to allow for the transfer of tag 150 through capsule 102 with an attached suture 118 but weak enough to be overcome by the radial engagement of springs 142 with detents 152 when locking sleeve 110 is retracted. Needle 126' has a slot 127' that preferably extends the entire length of needle 126' to allow for the needle sidewall to expand radially outwardly to release tag 150. The features of needle 126' that allow engagement with pusher 120 are not shown for purposes of clarity but are the same as those for needle 126. In this embodiment, however, locking sleeve 110 is retracted only from the distal end of needle 126' to allow for the release of tag 152 but not the release of needle 126' from pusher 120.

Operation of this embodiment is graphically illustrated in FIGS. 18A-18I. To begin operation this embodiment, suture 118 is secured to tag 150 via any number of conventional means as described above for the affixation of suture 118 to needle 126. The combination of tag 150 and suture 18 is then mounted in needle 126'. The needle/tag/suture assembly is advanced through locking sleeve 110 via pusher 120 in the same manner as described for needle 126 and as shown in FIG. 18B. Following the suction of a tissue fold into vacuum chamber 108, shown in FIG. 18A, the assembly is forced through tissue mound 95 and into distal tip 104 (FIG. 18C). Springs 142 engage detents 152 upon delivery of tag 152 into distal tip 104. Locking sleeve 110 is partially retracted from the distal end of needle 126' to allow for the release of tag 150. Needle 126' is retracted by proximally retracting pusher 120 in the manner described for needle 126 and as shown in FIG. 18D. The engaging surfaces of detents 152 and springs 142 overcome the frictional engagement of tag 150 to needle 126' and cause the sidewall of needle 126' to flex radially outwardly to release tag 150 which is retained in distal tip 104.

Upon retraction of needle 126' substantially proximal to vacuum chamber 108, suction is terminated to allow for the release of tissue mound 95 with suture 118 secured therein as shown in FIG. 18E. Needle 126' is then distally advanced into distal tip 104 to re-engage tag 150 as shown in FIG. 18F. Sliding sleeve 110 is advanced to an extreme distal position to allow for the capture of tag 150 within needle 126'. The combination of locking sleeve 110, needle 126', tag 150 and pusher 120 are retracted, preferably in unison by simultaneously retracting the pusher handle 122 and the locking sleeve handle to preferably retract the combination proximal to vacuum chamber 108 as shown in FIG. 18G. The process is then repeated with second tissue mound 95' as shown in FIGS. 18H and 18I. An alternate embodiment is shown in FIGS. 10A-10D in which the tag retaining features are eliminated in distal tip 104 and tags 150 are used as anchors, one per tissue mound. In this alternate embodiment, needle assembly is completely removed from the device to allow for additional tags 150 to be secured to the same suture. Once a desired number of tissue mounds have been sutured, the next step is to secure the suture and cinch the mounds together into a plication.

Figure 21:
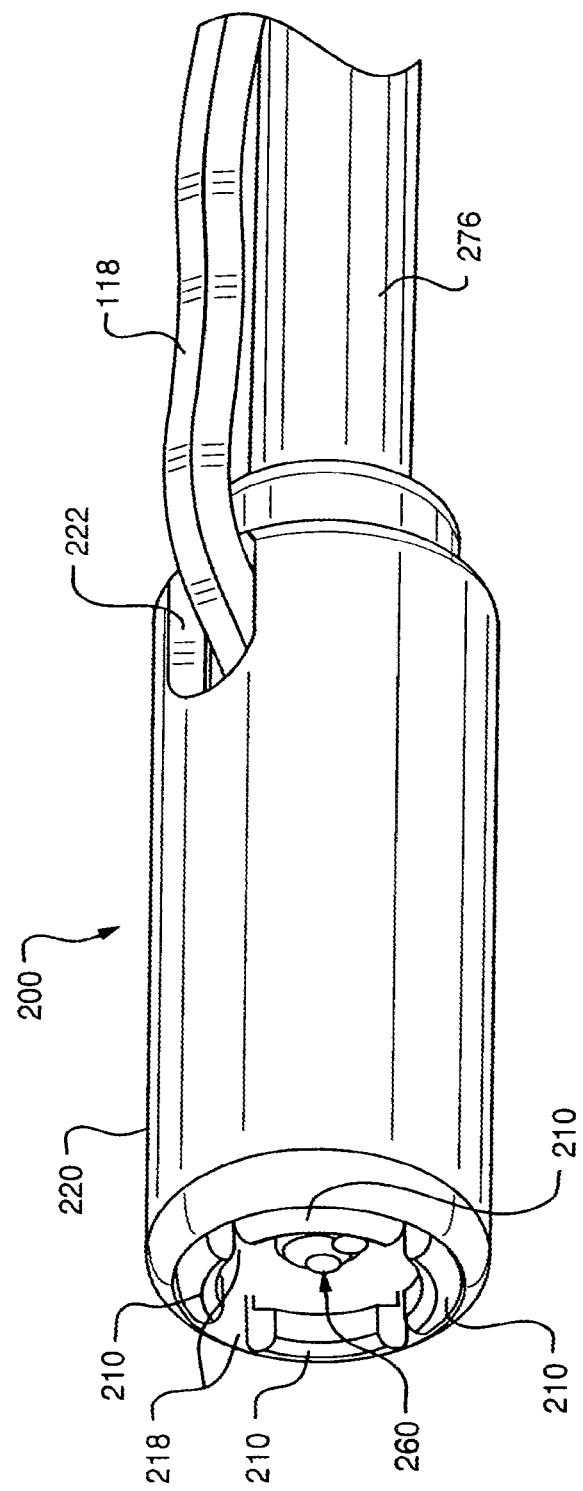
FIG. 21 is a side perspective view of a suture clip delivery device distal collet cage with a suture threaded through the collet cage according to one embodiment of the invention.
Figure 23:
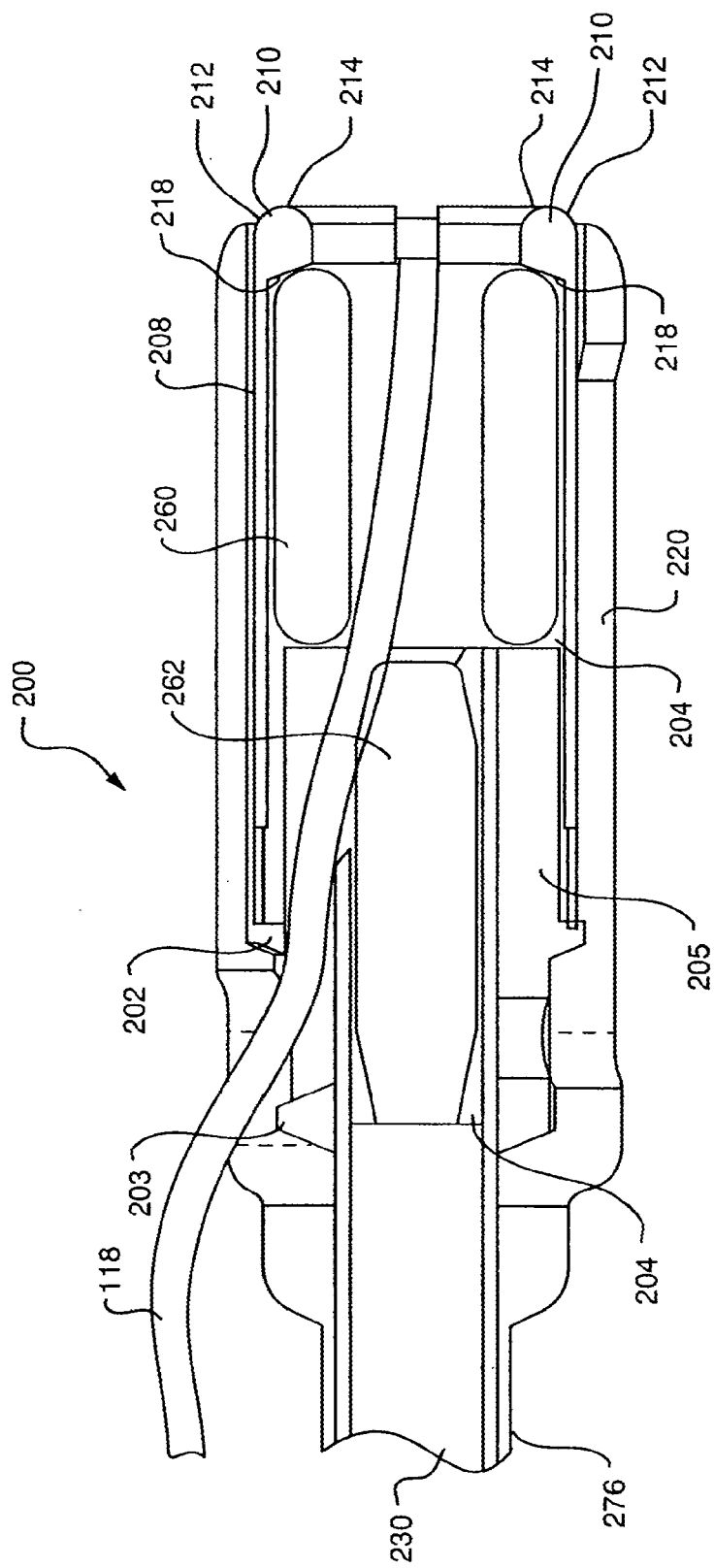
FIG. 23 is a side partial sectional view of a suture clip delivery device collet cage with a disassembled suture clip plug and ring and a suture threaded through the delivery device according to one embodiment of the invention.
Figure 24:
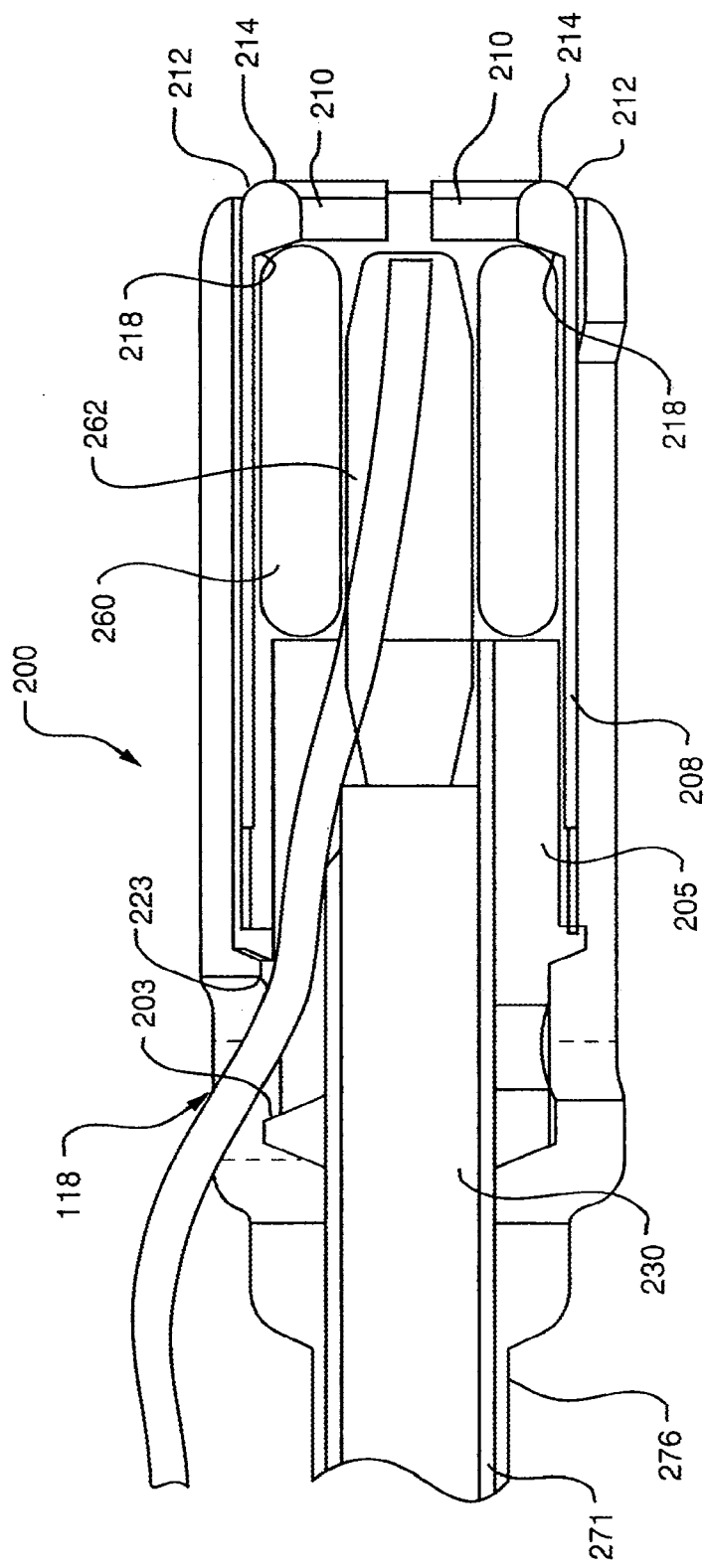
FIG. 24 is a side partial sectional view of a suture clip delivery device with a cinched suture clip according to one embodiment of the invention.

Referring to FIGS. 21, 23 and 24, the distal end of a suture clip delivery and locking catheter is shown generally as 200. Catheter distal end 200 is comprised primarily of a collet cage 202 to which the other components of distal end 200 are attached. Collet cage 202 is essentially a cylinder with two or more collet fingers 208 extending distally from a distal end of collet cage 202. When viewed from a distal end of collet cage 202, collet fingers 208 preferably form a segmented 360° ring. Extending radially inwardly from a distal end of each collet finger 208 is a collet finger flange 210 that functions as a stop to arrest distal advancement of a suture clip assembly loaded into collet cage 202. The combination of the distal end of collet cage 202, collet fingers 208 and distal flanges 210 define a cage within which the components of a suture clip are releasably encapsulated for delivery to a sutured tissue site. The cage further functions to align the suture clip components for assembly.

In a preferred embodiment, collet finger flanges 210 have radiused outer distal edges 212 to minimize trauma to a patient and radiused inner distal edges 214 to ease loading of suture clip components. In one embodiment (not shown), outer distal edges 212 extend radially outwardly beyond outer walls of collet finger 208 to function as a stop for an outer sliding sleeve 220 described below. Inner proximal faces of collet finger flanges 210 are oriented to a longitudinal axis of the collet fingers so that a plane occupied by flange proximal surfaces 216 forms an angle from about 90° to about 135° and preferably either 135° or 90° with 90° being the most preferred to maximize the stopping function.

Finger slots 218 are formed between and defined by collet fingers 208 and function as egress ports for sutures threaded through the components of a suture clip loaded into collet cage 202. Preferably, collet fingers 208 are biased in an open position so that radial force need only be applied to move the fingers from an open, suture clip loading/releasing position to a closed, suture clip confining position. Alternatively, finger collets 208 can be biased in a closed position as described in PCT Application No. PCT/US01/07349, the contents of which are incorporated herein by reference.

Situated within a hollow chamber defined by the inner walls of collet cage 202 is clip pusher 230 that freely slides within collet cage 202. Pusher 230 is adapted to be proximally advanced into registry with suture clip components to urge the components into engagement with suture 118. Pusher 230 can be a solid rod or a hollow cylinder such as a hypotube.

Situated in coaxial relationship with and freely sliding about collet cage 202 is outer sliding sleeve 220 that performs at least two functions; providing a radially inwardly directed force against collet fingers 208 to maintain the fingers in a closed position during suture clip delivery to a tissue site to minimize potential trauma that could be caused by open collet fingers and providing a means to sever the tail ends of a suture that has been secured with a suture clip. When advanced distally, sliding sleeve 220 encompasses collet fingers 208 and restricts radial movement of the fingers regardless whether the fingers are biased in an open or closed position. In this position, sliding sleeve 220 prevents premature opening of the collet.

Figure 25:
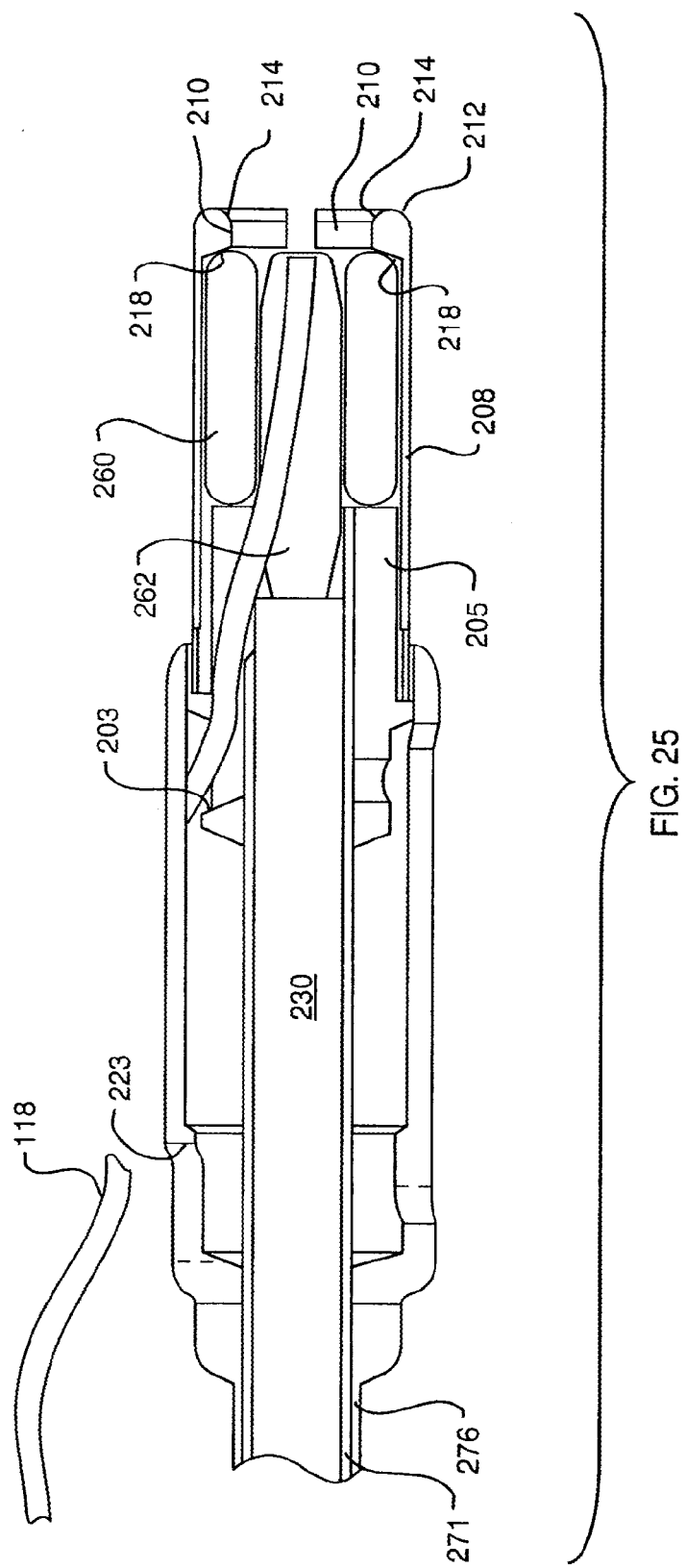
FIG. 25 is a side partial sectional view of a suture clip delivery device with a cinched suture clip and a severed suture according to one embodiment of the invention.

When proximally retracted, sliding sleeve 220 severs directly or cooperates with other components to sever suture material proximal to a cinched suture clip. In one embodiment shown in FIGS. 21-24, a suture slot 222 is formed in the sidewall of sliding sleeve 220 preferably in the area occupied by a proximal end of collet cage 202 when sliding sleeve 230 is in its distal most position. As shown in FIGS. 23-25, a collet cage cutting edge 203 is formed in a proximal end of sliding sleeve 220 at or near the distal end of collet cage 202 and extends radially outwardly toward sliding sleeve 220. As shown, a distal end 223 of suture slot 222 engages suture 118 and carries it toward a distal end of the body of collet cage 202. When the distal end 223 of suture slot 222 travels past cutting edge 203, suture 118 is pinched between the surfaces of suture slot 223 and cutting edge 203 that causes the suture to be severed as shown in FIG. 25.

At least one suture slot 223 is formed toward the distal end of sliding sleeve 30 to provide egress for excess suture material that typically extends beyond the orifice through which the catheter is inserted. It is preferred that finger slots 218 and suture slots 223 are at least partially aligned to allow a path for excess suture material to exit the suture clip delivery device. To accomplish alignment, an option alignment slot (not shown) can be formed preferably near a proximal end of sliding sleeve 30. An alignment pin (not shown) is optionally affixed to collet cage 202 and dimensioned to freely slide within the alignment slot. A version of this alignment feature is described and shown in PCT Application No. PCT/US01/07349.

The suture clips used in delivery device 200 are in the preferred form of a ring 260 and a plug 262. As shown in FIGS. 23-25, ring 260 is dimensioned to fit within collet cage 202 such that the concentricity of ring 260 is maintained with respect to the longitudinal axis of collet cage 202. Plug 262 is preferably of a headless design as shown and dimensioned to frictionally engage an inner wall of ring 260. Plug 262 is preferably formed with tapered ends to facilitate reception of suture 118, to ease insertion into ring 260 and to prevent abrasion of suture 118 between the ends of plug 262 and ring 260. Further details of suture clip components that can be used with delivery device 200 are disclosed in PCT Application No. PCT/US01/07349.

As will be appreciated, the cross-sectional diameter of plug 262 is smaller than the cross-sectional diameter of the outer wall of ring 260. Because of this necessary discrepancy in the dimensions of the suture clip components, accommodation is needed in collet cage 202 to ensure the concentricity of plug 262 when advanced distally into ring 260. One approach is to establish a reduced diameter portion in the proximal end of collet cage 202 to receive and maintain plug 262 in alignment with ring 260. In an alternate embodiment, shown in FIGS. 23-25, a generally cylindrical bushing 205 is provided in the proximal end of collet cage 202 to reduce the complexity of the geometry of the inner walls of collet cage 202. Bushing 205 is adapted to allow for the free axial movement of plug 262 within collet cage 202.

Figure 26:
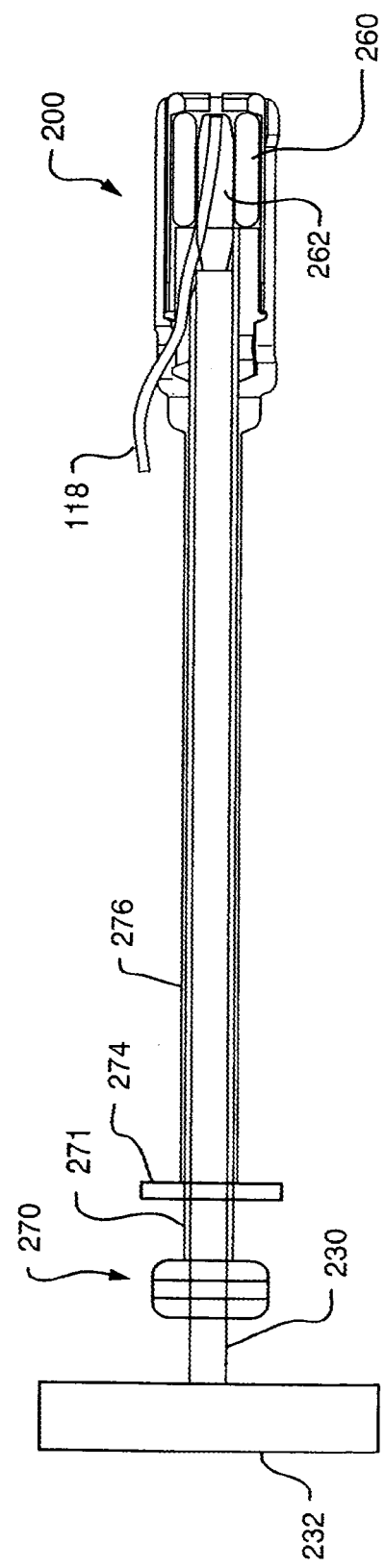
FIG. 26 is a side view of a suture clip delivery device including collet cage and handle assembly with a suture threaded through the collet cage and a sliding cutter handle in a distal position according to one embodiment of the invention.
Figure 27:
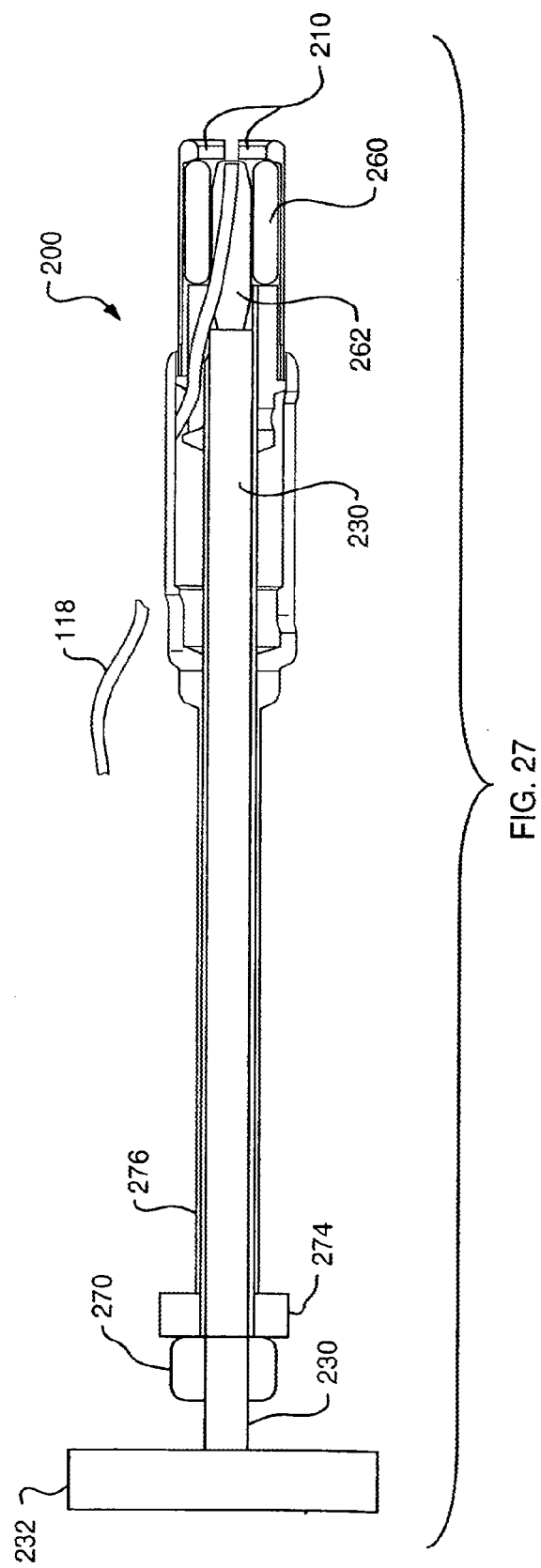
FIG. 27 is a side view of a suture clip delivery device including collet cage and handle assembly with a suture threaded through the collet cage and severed and with a sliding clutter handle in a retracted position.

The overall configuration of the suture clip delivery device is shown in FIGS. 26 and 27. A control handle 270 is attached to a proximal end of a collet cage tube 271 that may be in the form of a hypotube. A distal end of tube 271 is attached to the proximal end of collet cage 202. Tube 271 has an inner diameter that is adapted to receive clip pusher 230 that slides freely within tube 271. To operate the working features of the delivery device, two control surfaces are provided for advancing and retracting the various sliding components. The first, clip pusher handle 232, is attached to the proximal end of clip pusher 230. The second is sliding sleeve handle 274 which is attached to a proximal end of a sliding sleeve tube 276, the distal end of which comprises sliding sleeve 220. Sliding sleeve tube 276 may be in the form of a hypotube with an inner diameter dimensioned to receive collet cage tube 271 that slides freely within sliding sleeve tube 276. Clip pusher 230, collet cage tube 271 and sliding sleeve tube 276 are all coaxially arranged to allow the system to be dimensioned to slide freely within the working channel of endoscope 90 and the needle assembly channel of capsule 102.

To operate the suture clip delivery device, clip pusher handle 232 and sliding sleeve handle 274 are retracted to allow collet fingers 208 to spring radially outwardly to receive the suture clip components, plug 262 and ring 260. Next, suture 118 previously placed into a plurality of tissue mounds is threaded through ring 260, collet cage 202 and out suture slot 222. The ends of the suture are maintained out of the delivery device and endoscope 90.

Figure 22:
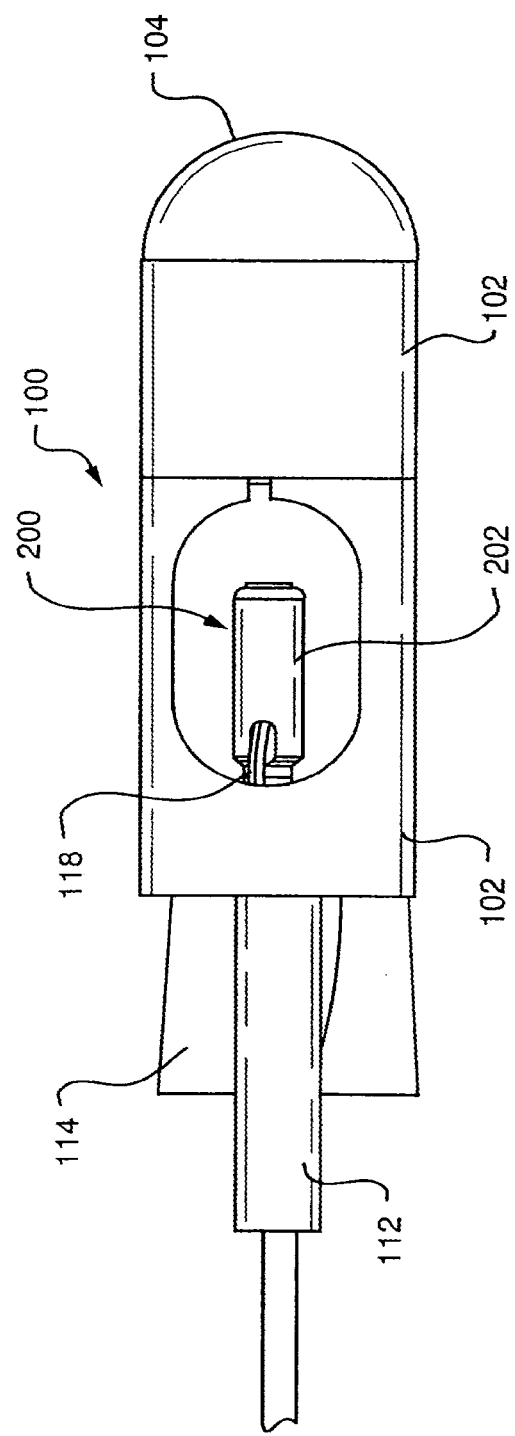
FIG. 22 is a top plan view of a suture capsule with a suture clip delivery device advanced through the capsule.

With the suture threaded through the suture clip delivery device, the device is distally advanced through the working channel of endoscope 90, into the proximal end of capsule 102 and into vacuum chamber 108 as shown in FIGS. 18J, 18K and 22. The device is now in a position to begin the suture cinching procedure. Because of inherent flexibility in the device, collet cage 202 may slightly rotate out of axial alignment with the longitudinal axis of capsule 102 toward the sutured tissue mounds via the tension created by suture 118. This is a desired effect as it allows the distal end of collet cage 202 to come into closer proximity to the last tissue mound sutured. This maximizes the potential to provide a tight plication since suture slack can be minimized. In short, the tissue mounds can be cinched closer together the closer collet cage 202 can be situated to the tissue mounds.

Figure 11:
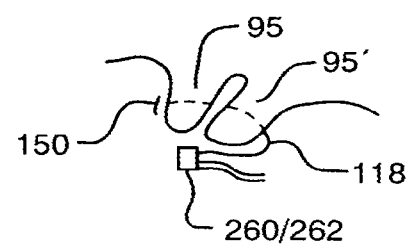
FIG. 11 is a side elevational view of a tissue plication with a suture piercing the plication mound halves and secured with a suture clip.
Figure 13:
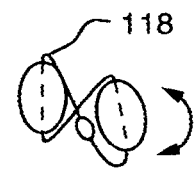
FIG. 13 is a tissue plication secured with a suture clip according to one embodiment of the invention.
Figure 14:
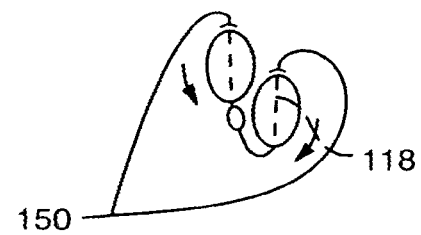
FIG. 14 is a tissue plication secured with a suture clip according to another embodiment of the invention.

The cinching process begins by providing a distally directed force onto clip pusher handle 232. This causes the forward advancement of pusher 230 into registration with the proximal end of plug 262 that, in turn, is urged distally into ring 260 to thereby capture suture 118 via the frictional engagement of plug 262 to ring 260. Once plug 262 has been preferably fully engaged to ring 260, sliding sleeve handle 274 can be proximally retracted to sever the excess suture 118 and to allow collet fingers 208 to flex radially outwardly to allow for the release of the cinched suture clip as shown in FIG. 18L. The plication formed according to the procedure described herein forms a FIG. 8 suture pattern with an attached suture clip as shown in FIG. 13. FIGS. 11 and 14 show a plication formed with the use of tag 150 as an anchor with twists in the tissue mounds and suture paths shown with directional arrows. The delivery device can then be retracted out of capsule 102 and endoscope 90 to end the procedure or to prepare for another cycle of suturing and suture cinching. At all times during the procedure or multiple cycles of the procedures described herein, endoscope 90 and capsule 102 can be maintained in the patient with a single intubation event. Endoscope is simply maneuvered to the desired tissue locations to perform the gastroplasty procedure.

It should be understood that the foregoing description of the invention is intended merely to be illustrative thereof and that other modifications, embodiments and equivalents may be apparent to those who are skilled in the art without departing from its spirit.

What is claimed is:

1. A method of treating obesity, the method comprising:
endoscopically forming at least one plication in a stomach using an endoscope by performing acts of:
(a) endoscopically suturing stomach tissue with at least one suture using an endoscopic suturing device during an endoscopic intubation of the endoscope; and
(b) endoscopically securing the suture to the stomach tissue with an endoscopic suture securing device during the same endoscopic intubation of the endoscope to thereby maintain the at least one plication.

2. The method according to claim 1, wherein act (a) includes collecting stomach tissue with the endoscopic suturing device, and sewing the collected stomach tissue with the suture.

3. The method according to claim 2, wherein the endoscopic suturing device includes a capsule adapted to collect tissue, and act (a) includes collecting stomach tissue with the capsule.

4. The method according to claim 3, wherein the capsule includes a suction port, and act (a) includes suctioning stomach tissue into the capsule through the suction port.

5. The method according to claim 1, wherein the endoscopic suturing device includes a needle with the suture being attached to the needle, and act (a) includes advancing the needle and the suture through the collected stomach tissue.

6. The method according to claim 5, wherein act (b) includes inserting the endoscopic suture securing device into the endoscopic suturing device.

7. The method according to claim 6, wherein act (b) includes removing the needle from the endoscopic suturing device and subsequently inserting the endoscopic suture securing device into the endoscopic suturing device to secure the suture.

8. The method according to claim 1, wherein act (b) includes securing the suture with a suture clip delivered with the endoscopic suture securing device.

9. The method according to claim 8, wherein act (b) includes releasing the suture clip from the endoscopic suture securing device after securing the suture.

10. The method according to claim 1, wherein act (b) includes inserting the endoscopic suture securing device through the endoscope.

* * * * *